US008801622B2

United States Patent
Baker, Jr.

(10) Patent No.: US 8,801,622 B2
(45) Date of Patent: *Aug. 12, 2014

(54) SYSTEM AND METHOD FOR PULSE RATE CALCULATION USING A SCHEME FOR ALTERNATE WEIGHTING

(75) Inventor: Clark R. Baker, Jr., Newman, CA (US)

(73) Assignee: Covidien LP, Mansfield, MA (US)

(*) Notice: Subject to any disclaimer, the term of this patent is extended or adjusted under 35 U.S.C. 154(b) by 637 days.

This patent is subject to a terminal disclaimer.

(21) Appl. No.: 13/041,991

(22) Filed: Mar. 7, 2011

(65) Prior Publication Data

US 2011/0152652 A1  Jun. 23, 2011

Related U.S. Application Data

(63) Continuation of application No. 11/528,862, filed on Sep. 28, 2006, now Pat. No. 7,922,665.

(51) Int. Cl.
*A61B 5/02* (2006.01)

(52) U.S. Cl.
USPC .......................... 600/500; 600/502; 600/504

(58) Field of Classification Search
USPC .................. 600/481, 490, 500–502, 504–507
See application file for complete search history.

(56) References Cited

U.S. PATENT DOCUMENTS

| 3,638,640 | A | 2/1972 | Shaw |
|---|---|---|---|
| 4,714,341 | A | 12/1987 | Hamaguri et al. |
| 4,800,495 | A | 1/1989 | Smith |
| 4,805,623 | A | 2/1989 | Jöbsis |
| 4,807,631 | A | 2/1989 | Hersh et al. |
| 4,859,057 | A | 8/1989 | Taylor et al. |
| 4,863,265 | A | 9/1989 | Flower et al. |
| 4,901,238 | A | 2/1990 | Suzuki et al. |
| 4,911,167 | A | 3/1990 | Corenman et al. |
| 4,936,679 | A | 6/1990 | Mersch |
| 4,972,331 | A | 11/1990 | Chance |
| 5,099,841 | A | 3/1992 | Heinonen et al. |
| 5,119,815 | A | 6/1992 | Chance |
| 5,122,974 | A | 6/1992 | Chance |

(Continued)

FOREIGN PATENT DOCUMENTS

| DE | 102 13 692 A1 | 10/2003 |
|---|---|---|
| JP | 5-212016 | 8/1993 |

(Continued)

OTHER PUBLICATIONS

Bongard, Frederic S., et al., "Continuous Dual Oximetry in Surgical critical care—Indications and Limitations," *Annals of Surgery*, vol. 216, No. 1, pp. 60-68 (1992).

(Continued)

*Primary Examiner* — Michael D'Angelo
(74) *Attorney, Agent, or Firm* — Fletcher Yoder, P.C.

(57) ABSTRACT

Embodiments of the present invention relate to a method for analyzing pulse data. In one embodiment, the method comprises receiving a signal containing data representing a plurality of pulses, the signal generated in response to detecting light scattered from blood perfused tissue. Further, one embodiment includes performing a pulse identification or qualification algorithm on at least a portion of the data, the pulse identification or qualification algorithm comprising at least one constant, and modifying the at least one constant based on results obtained from performing the pulse identification or qualification algorithm, wherein the results indicate that a designated number of rejected pulses has been reached.

20 Claims, 8 Drawing Sheets

(56) References Cited

U.S. PATENT DOCUMENTS

| | | |
|---|---|---|
| 5,167,230 A | 12/1992 | Chance |
| 5,190,038 A | 3/1993 | Polson et al. |
| 5,297,548 A | 3/1994 | Pologe |
| 5,299,120 A | 3/1994 | Kaestle |
| 5,349,519 A | 9/1994 | Kaestle |
| 5,355,880 A | 10/1994 | Thomas et al. |
| 5,372,136 A | 12/1994 | Steuer et al. |
| 5,385,143 A | 1/1995 | Aoyagi |
| 5,398,680 A | 3/1995 | Polson et al. |
| 5,482,036 A | 1/1996 | Diab et al. |
| 5,553,614 A | 9/1996 | Chance |
| 5,564,417 A | 10/1996 | Chance |
| 5,575,285 A | 11/1996 | Takanashi et al. |
| 5,595,176 A | 1/1997 | Yamaura |
| 5,630,413 A | 5/1997 | Thomas et al. |
| 5,645,059 A | 7/1997 | Fein et al. |
| 5,645,060 A | 7/1997 | Yorkey |
| 5,662,105 A | 9/1997 | Tien |
| 5,692,503 A | 12/1997 | Kuenstner |
| 5,752,920 A * | 5/1998 | Ogura et al. ............ 600/494 |
| 5,758,644 A | 6/1998 | Diab et al. |
| 5,766,127 A | 6/1998 | Pologe et al. |
| 5,779,631 A | 7/1998 | Chance |
| 5,820,550 A | 10/1998 | Polson et al. |
| 5,830,139 A | 11/1998 | Abreu |
| 5,842,981 A | 12/1998 | Larsen et al. |
| 5,853,364 A | 12/1998 | Baker, Jr. et al. |
| 5,873,821 A | 2/1999 | Chance et al. |
| 5,995,856 A | 11/1999 | Mannheimer et al. |
| 6,002,952 A | 12/1999 | Diab et al. |
| 6,011,986 A | 1/2000 | Diab et al. |
| 6,064,898 A | 5/2000 | Aldrich |
| 6,067,462 A | 5/2000 | Diab et al. |
| 6,083,157 A | 7/2000 | Noller |
| 6,120,460 A | 9/2000 | Abreu |
| 6,134,460 A | 10/2000 | Chance |
| 6,163,715 A | 12/2000 | Larsen et al. |
| 6,181,958 B1 | 1/2001 | Steuer et al. |
| 6,230,035 B1 | 5/2001 | Aoyagi et al. |
| 6,266,546 B1 | 7/2001 | Steuer et al. |
| 6,312,393 B1 | 11/2001 | Abreu |
| 6,393,311 B1 | 5/2002 | Edgar, Jr. et al. |
| 6,397,091 B2 | 5/2002 | Diab et al. |
| 6,415,236 B2 | 7/2002 | Kobayashi et al. |
| 6,438,399 B1 | 8/2002 | Kurth |
| 6,463,311 B1 | 10/2002 | Diab |
| 6,487,439 B1 | 11/2002 | Skladnev et al. |
| 6,501,974 B2 | 12/2002 | Huiku |
| 6,501,975 B2 | 12/2002 | Diab et al. |
| 6,519,486 B1 | 2/2003 | Edgar, Jr. et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,591,122 B2 | 7/2003 | Schmitt |
| 6,594,513 B1 | 7/2003 | Jobsis et al. |
| 6,606,509 B2 | 8/2003 | Schmitt |
| 6,615,064 B1 | 9/2003 | Aldrich |
| 6,622,095 B2 | 9/2003 | Kobayashi et al. |
| 6,658,277 B2 | 12/2003 | Wasserman |
| 6,662,030 B2 | 12/2003 | Khalil et al. |
| 6,671,526 B1 | 12/2003 | Aoyagi et al. |
| 6,671,528 B2 | 12/2003 | Steuer et al. |
| 6,675,031 B1 | 1/2004 | Porges et al. |
| 6,678,543 B2 | 1/2004 | Diab et al. |
| 6,690,958 B1 | 2/2004 | Walker et al. |
| 6,699,194 B1 | 3/2004 | Diab et al. |
| 6,708,048 B1 | 3/2004 | Chance |
| 6,711,424 B1 | 3/2004 | Fine et al. |
| 6,711,425 B1 | 3/2004 | Reuss |
| 6,721,584 B2 | 4/2004 | Baker, Jr. et al. |
| 6,785,568 B2 | 8/2004 | Chance |
| 6,801,797 B2 | 10/2004 | Mannheimer et al. |
| 6,801,799 B2 | 10/2004 | Mendelson |
| 6,810,277 B2 | 10/2004 | Edgar, Jr. et al. |
| 6,816,741 B2 * | 11/2004 | Diab ............................. 600/324 |
| 6,873,865 B2 | 3/2005 | Steuer et al. |
| 6,949,081 B1 | 9/2005 | Chance |
| 6,961,598 B2 | 11/2005 | Diab |
| 6,996,427 B2 | 2/2006 | Ali et al. |
| 7,016,715 B2 | 3/2006 | Stetson |
| 7,024,233 B2 | 4/2006 | Ali et al. |
| 7,027,849 B2 | 4/2006 | Al-Ali |
| 7,072,702 B2 | 7/2006 | Edgar, Jr. et al. |
| 7,254,433 B2 | 8/2007 | Diab et al. |
| 7,489,958 B2 | 2/2009 | Diab et al. |
| 7,499,740 B2 * | 3/2009 | Nordstrom et al. ........... 600/323 |
| 7,499,741 B2 | 3/2009 | Diab et al. |
| 7,689,259 B2 * | 3/2010 | Mannheimer et al. ........ 600/323 |
| 7,729,733 B2 * | 6/2010 | Al-Ali et al. ................... 600/310 |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0128544 A1 | 9/2002 | Diab et al. |
| 2002/0133068 A1 | 9/2002 | Huiku |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0097797 A1 | 5/2004 | Porges et al. |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0080323 A1 | 4/2005 | Kato |
| 2005/0101850 A1 | 5/2005 | Parker |
| 2005/0107676 A1 | 5/2005 | Acosta et al. |
| 2005/0113656 A1 | 5/2005 | Chance |
| 2005/0168722 A1 | 8/2005 | Forstner et al. |
| 2005/0192488 A1 | 9/2005 | Bryenton et al. |
| 2005/0197552 A1 * | 9/2005 | Baker, Jr. ..................... 600/324 |
| 2005/0203357 A1 | 9/2005 | Debreczeny et al. |
| 2005/0267346 A1 | 12/2005 | Faber et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0030764 A1 | 2/2006 | Porges et al. |
| 2006/0052680 A1 | 3/2006 | Diab |
| 2006/0058683 A1 | 3/2006 | Chance |
| 2008/0036752 A1 | 2/2008 | Diab et al. |

FOREIGN PATENT DOCUMENTS

| | | |
|---|---|---|
| WO | WO 92/20273 | 11/1992 |
| WO | WO 94/03102 | 2/1994 |
| WO | WO 97/49330 | 12/1997 |
| WO | WO 01/45553 A1 | 6/2001 |
| WO | WO2007/013708 | 2/2007 |

OTHER PUBLICATIONS

Lee, Jason C.S., et al., "Measurement of Percent Carboxyhemoglobin with Pulse-Oximetry Technique," *IEEE Engi-*

(56) References Cited

OTHER PUBLICATIONS neering in Medicine & Biology Society 10$^{th}$ Annual International Conference, CH2566-88, vol. 88, pp. 1781-1782 (1988).

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093, Nov. 12, 1989.

* cited by examiner

SYSTEM AND METHOD FOR PULSE RATE CALCULATION USING A SCHEME FOR ALTERNATE WEIGHTING

This application is a continuation of U.S. patent application Ser. No. 11/528,862, by Clark R. Baker, Jr, entitled "System and Method for Pulse Rate Calculation Using a Scheme for Alternate Weighting", filed on Sep. 28, 2006, which is hereby incorporated by reference in its entirety.

TECHNICAL FIELD

This invention relates generally to the field of medical devices and, more particularly, to adjusting constants (e.g., thresholds and coefficients) used in pulse oximetry analysis algorithms based on performance criteria.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

A pulse oximeter is a medical device that may be used to measure various blood characteristics such as oxygen saturation of hemoglobin in pulsing blood and/or a patient's pulse rate. To measure these characteristics, a non-invasive sensor may be used to pass light through a portion of blood perfused tissue (e.g., a finger, earlobe, or toe) and photo-electrically sense the absorption and scattering of light in the tissue. The amount of light absorbed and/or scattered is analyzed to estimate the amount of blood constituent in the tissue.

A detector signal resulting from measurement of the light absorbed and/or scattered by the blood perfused tissue includes information that describes the blood characteristics. As an example, pulses refer to the varying amount of arterial blood present in the tissue during a cardiac cycle. The varying amount of arterial blood yields cyclic attenuation of the light passing through the tissue. Accordingly, the detector signal from measurement of the light exhibits the familiar plethysmographic waveform representative of the cardiac cycle.

Analysis of detector signals involves processes that use various parameters. As an example, an analysis may involve filtering estimates of hemoglobin saturation to improve the accuracy of the saturation estimates. As another example, the analysis may involve filtering of plethysmographic waveforms. The filtering may use parameters such as filter weights or coefficients to adjust the filtering process. As another example, the analysis may involve applying pulse qualification criteria to qualify or disqualify pulses. The pulse qualification criteria may include parameters used to adjust the pulse qualification.

Under challenging conditions, it can be difficult to discern a valid arterial pulse from detector signals when using established pulse oximetery systems and methods. For example, under certain circumstances, pulse waveforms may be distorted by noise, which may make it difficult to discern a valid pulse among the distortions. Accordingly, it is desirable to provide a flexible and robust system and method for detecting valid arterial pulse signals when experiencing challenging conditions.

BRIEF DESCRIPTION OF THE DRAWINGS

Certain exemplary embodiments are described in the following detailed description and in reference to the drawings in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The exemplary embodiments described below are best understood by referring to FIGS. 1 through 8 of the drawings, wherein like numerals are used for like and corresponding parts of the various drawings. The methods and systems in accordance with these exemplary embodiments are directed towards adjusting parameters of oximetry analysis. These embodiments may be particularly applicable to pulse oximeter monitors and pulse oximetry sensors and, thus, are explained by reference to measuring oxygen saturation and qualifying pulses. It should be realized, however, that the embodiments may be applicable to other patient monitors and associated patient sensors, such as, for example, an electrocardiograph (ECG), blood pressure monitor, etc., and are, thus, also applicable to nonoximetry methods and systems.

Figure 1:
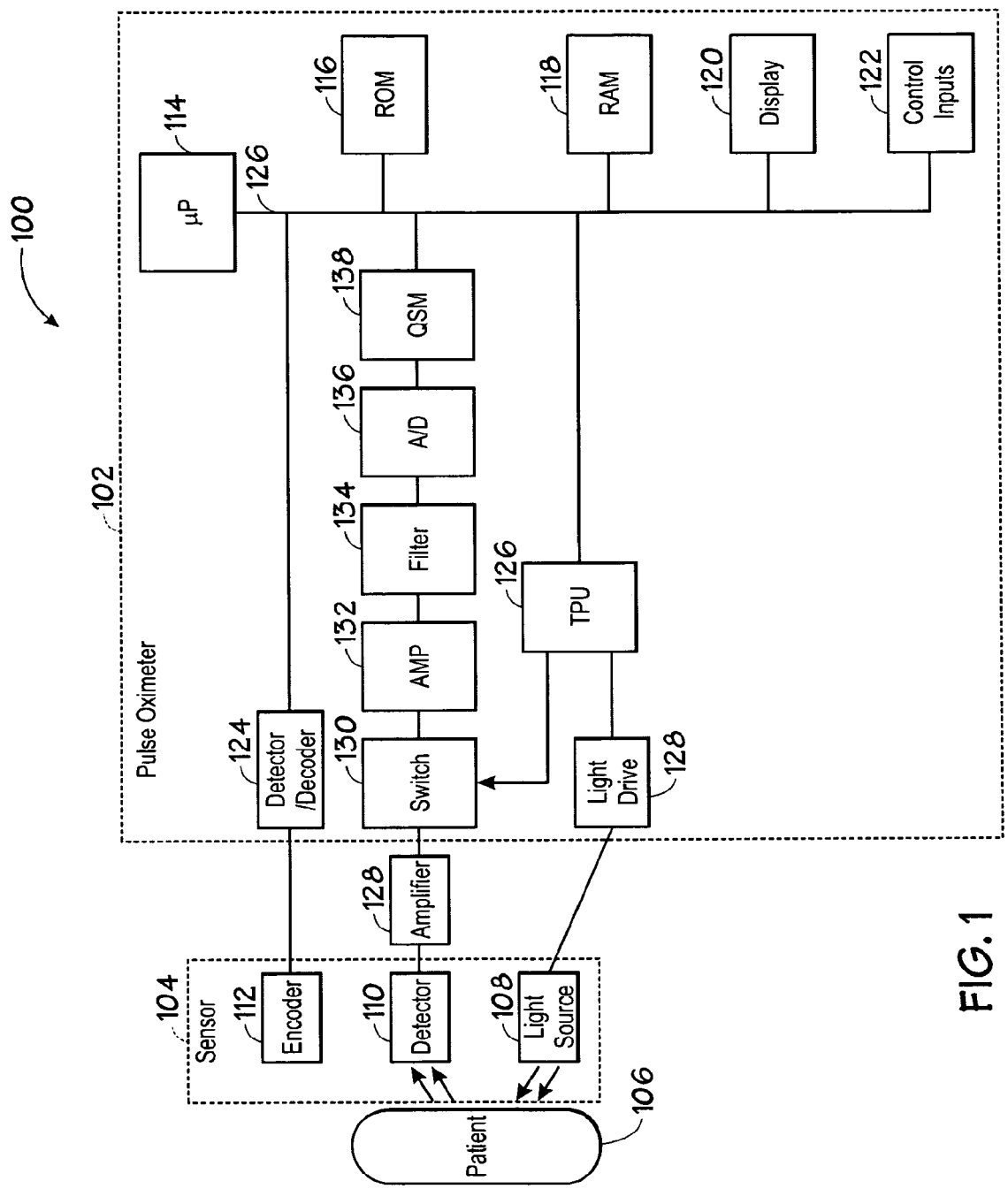
FIG. 1 is a block diagram of one embodiment of a pulse oximeter system that is configured to implement certain techniques in accordance with the present invention.

FIG. 1 is a block diagram of one embodiment of a pulse oximeter system 100 that is configured to implement certain techniques in accordance with the present invention. The pulse oximeter system 100 may include a pulse oximeter 102 wherein one or more components of the oximeter 102 may include appropriate input devices, output devices, mass storage media, processors, memory, or other components for receiving, processing, storing, and communicating information according to the operation of the pulse oximeter 102. Additionally, the pulse oximeter system 100 may include a sensor 104 in electronic communication with the oximeter 102. In the illustrated embodiment, the oximeter 102 operates in conjunction with the sensor 104 to obtain blood characteristic readings from a patient 106.

As discussed in detail below, the pulse oximeter system 100 is configured to identify and qualify a patient's blood flow pulses using algorithms that may be referred to as pulse identification or qualification algorithms. These pulse identification algorithms implement variable constants or weighting factors to facilitate pulse detection during challenging detection conditions. For example, during challenging data acquisition conditions, an initial set of constants in the algorithms may be switched with alternative constants based on a count of consecutive rejected and qualified pulses. This use of alternative constants has been demonstrated to reduce pulse rate dropouts (i.e., failed pulse readings) while maintaining or improving pulse accuracy under certain challenging conditions.

A specific example of providing alternative constants in algorithms is provided herein. It should be noted that while the embodiments discussed in detail below utilize specific constant values and equations, other embodiments may utilize different constant values and different equations in a manner in accordance with embodiments of the present invention. For example, while in one embodiment, a primary constant value has a specific alternative value, one of ordinary skill in the art will recognize that different values based on different data may be implemented as primary and alternative constants, and that a plurality of alternative constants may be used based on the data.

Turning to FIG. 1, the sensor 104 may include, a light source 108, a photodetector 110, and an encoder 112. It should be noted that in some embodiments, multiple light sources 108 are used. In operation, the sensor 104 illuminates the blood perfused tissue 106, detects light scattered by the tissue 106, and generates detector signals. Specifically, the scattered light is detected by the photodetector 110, which then generates detector signals representative of the detected light. The generated detector signals are supplied to the oximeter 102 for analysis. Further, the encoder 112 provides the oximeter 102 with signals indicative of the wavelength of light source 108 to allow the oximeter 102 to select appropriate calibration coefficients for calculating parameters such as oxygen saturation, for example.

The pulse oximeter 102 utilizes various oximeter components to analyze the detector signals, control the acquisition of blood characteristic data, and facilitate data access. For example, in the illustrated embodiment, the pulse oximeter 102 includes general processing and interface components such as a microprocessor 114, a ROM 116, a RAM 118, a display 120, control inputs 122, and a detector/decoder 124, coupled to an internal bus 126. The microprocessor 114 calculates oxygen saturation based on the values of signals received from the sensor 104 and certain corresponding weighting coefficients. The ROM 116 stores the coefficients used in the calculations, and the detector/decoder 124 selects the appropriate coefficients according to signals received from the encoder 112. The control inputs 122 are components configured to receive input data and instructions. For instance, the control inputs 122 may include a switch on the pulse oximeter, a keyboard, or a port configured to provide instructions from a remote host computer. The display 120 (e.g., a computer monitor) provides feedback and results of the analysis.

The pulse oximeter 102 also includes components that operate to control the light that passes through the tissue 106. For example, in the illustrated embodiment, the pulse oximeter 102 may include a time processing unit (TPU) 126 and light drive circuitry 128. The TPU 126 is configured to provide timing control signals to the light drive circuitry 128, which controls when the light source 108 is illuminated. Additionally, in some embodiments that utilize multiple light sources 108, the drive circuitry 128 controls multiplexed timing.

During system operation, signals from the detector 110 are received for processing by the pulse oximeter 102 through an amplifier 128. The pulse oximeter 102 includes several components that operate to process the received signals. Specifically, in the illustrated embodiment, the pulse oximeter 102 includes a switching circuit 130, an amplifier 132, a low pass filter 134, an analog-to-digital converter 136, and a queued serial module (QSM) 138. The switching circuit 130 controls the sampling of the signals in response to instructions from TPU 126. For example, sampling times may be set to predetermined or calculated values. If multiple light sources are used, the sampling times may depend upon which of the light sources 108 are illuminated.

The signals from the switching circuit 130 are passed through the amplifier 132, the low pass filter 134, and the analog-to-digital converter 136. Digital data from the detector signals is then stored in the QSM 138. Further, the digital data may be downloaded to the RAM 118 as the QSM 138 is filled. In some embodiments, analog data may be stored before converting it to digital data. Further, in some embodiments, there may be multiple parallel paths of separate amplifiers, filters, and analog-to-digital converters corresponding to different light wavelengths.

Figure 2:
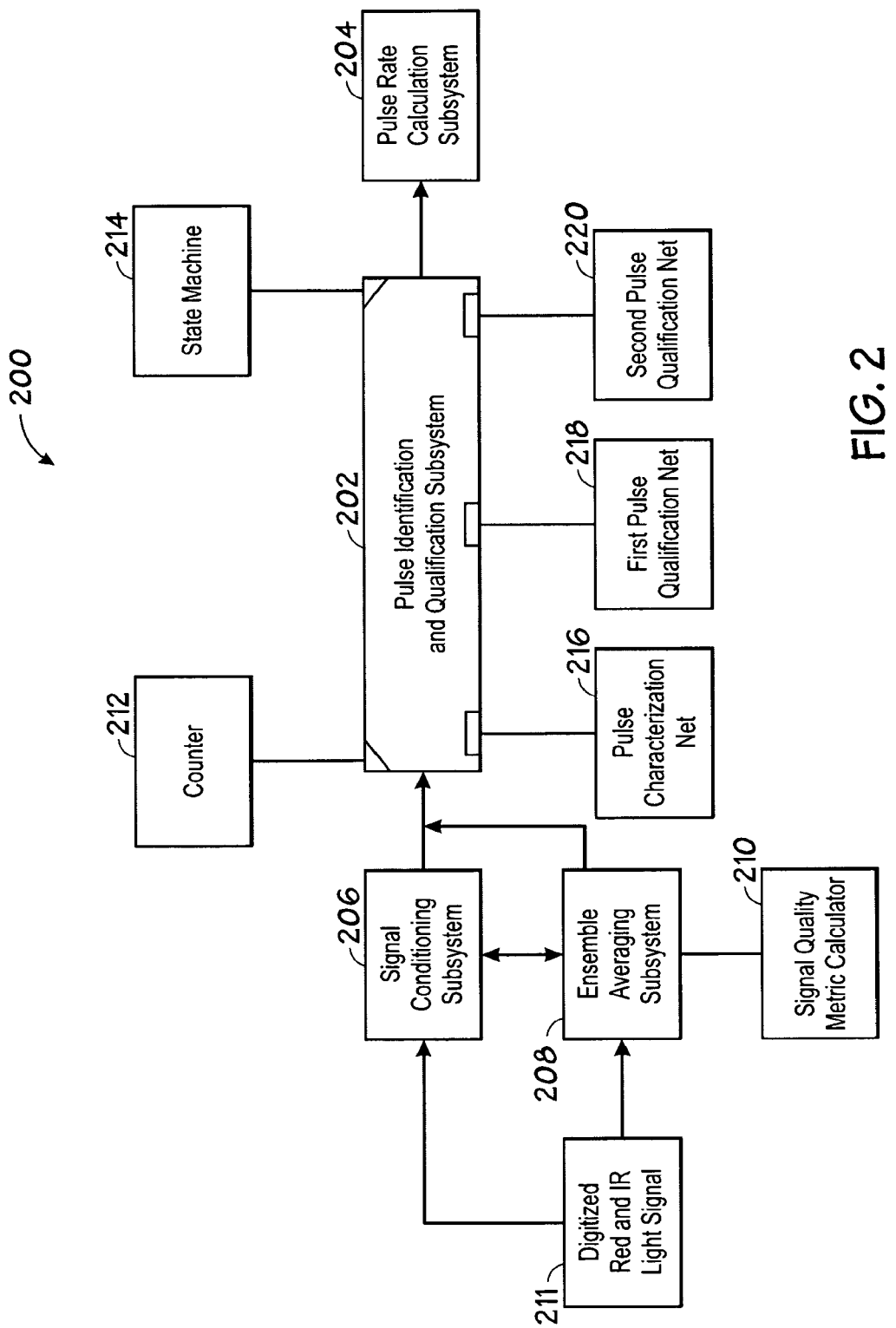
FIG. 2 is a block diagram of a signal processing architecture of a pulse oximeter in accordance with an exemplary embodiment of the present invention.

FIG. 2 is a block diagram of a signal processing architecture 200 of a pulse oximeter in accordance with an exemplary embodiment of the present invention. The signal processing architecture 200 may be implemented as a software process that is executed by a processor of a pulse oximeter, such as the processor 114 of the oximeter 102 discussed above. The processing architecture 200 may include a pulse identification and qualification subsystem 202, a pulse rate calculation signal conditioning subsystem 206, an ensemble averaging subsystem 208, and a signal quality metric calculator 210.

The pulse identification and qualification subsystem (PIQS) 202 of the illustrated embodiment is configured to identify potential pulses and qualify the potential pulses as likely or unlikely arterial pulses. Additionally, the PIQS 202 is configured to detect the presence of noise, indicate the occurrence of individual pulses, and provide descriptive metrics used by other subsystems to fine-tune oximeter performance. In operation, the PIQS 202 utilizes various algorithms to process waveforms received from a patient. This processing by the PIQS 202 may be divided into several parts. For example, a first part may include identifying pulses by finding maximum and minimum phases. A second part may include detecting partial pulse events (e.g., noise and dicrotic notches) and concatenating the detected partial pulse events into a complete pulse. A third part may include qualifying pulses and rejecting potential pulses that are unsuitable for pulse-rate calculation.

The PIQS 202 is configured to operate during challenging conditions. For example, the PIQS 202 facilitates pulse detection and identification of qualified pulses while encountering arrhythmias, rapid changes in pulse rate, motion, low perfusion (poor signal-to-noise ratio), respiratory artifact, and unusually shaped pulses from test devices. In operation, the PIQS 202 may detect a potential pulse as a waveform having a maximum phase followed by a minimum phase. Once detected, a potential pulse is ignored by the PIQS 202 if it is deemed to be an artifact of the pulse shape, such as a dicrotic notch. If the pulse is not designated as an artifact, the PIQS 202 treats the potential pulse as a "pulse" that is either "qualified" or "rejected." The PIQS 202 then provides qualified pulses to the pulse rate calculation subsystem (PRCS) 204 for pulse-rate estimation. The PIQS 202 may output a pulse quality of individual pulses, a degree of arrhythmia, pulse amplitude variations, and/or qualified pulse periods and age.

The optical waveform produced by human pulses typically falls faster than it rises, and the DC level does not change significantly on a pulse-to-pulse basis. This asymmetry is more pronounced at low pulse rates. In accordance with present embodiments, the PIQS 202 operates under an assumption that its input waveforms have been highpass filtered, which makes the upstroke a long plateau and the downstroke a brief, sharp minima, so that the highpass-filtered pulse has a pronounced negative skew. It should be noted that a highpass filter (e.g., a derivative filter) may be deemed to provide sufficient AC-coupling to substantially eliminate baseline shifts between pulses such that its output is generally zero-mean.

The PIQS 202 may receive input waveforms that have been pre-processed by the signal conditioning subsystem (SCS) 206. In the illustrated embodiment, the SCS 206 is configured to receive digitized Red and IR light signals 211 and output pre-processed Red and IR signals. Specifically, in operation, the SCS 206 conditions signals to emphasize higher frequencies associated with a human plethysmograph and to attenuate lower frequencies associated with interference from noise sources. For example, the SCS 206 may condition received signals by taking a first derivative to reduce or eliminate a baseline shift and then low pass filter the signals with coefficients based on hardware characteristics. It should be noted that derivative-filtered plethysmographs characteristically have a negative skewness. The signal conditioning subsystem 206 may also divide the lowpass filtered values by the average of the respective IR or Red signals.

The waveforms received by the PIQS 202 may also be pre-processed by the ensemble averaging system (EAS) 208. Indeed, in the illustrated embodiment, both the SCS 206 and/or the EAS 208 can pre-process the waveforms provided to the PIQS 202. The EAS 208 incorporates a low pass filter. In operation, the EAS 208 may receive normalized pre-processed Red and IR signals, average pulse period, and/or low pass filter weighs and ensemble averaging filter weights provided by the signal quality metrics calculator (SQMC) 210. The EAS 208 ensemble averages and filters the normalized and preprocessed signals from the SQMC 210. The EAS 208 then outputs filtered Red and IR signals and/or age. Additionally, the EAS 208 may track the age of the signal and/or filtering results. It should be noted that ensemble averaging may involve attenuating frequencies that are not of interest. For example, ensemble averaging may involve attenuating frequencies that are not at the estimated pulse rate or harmonic.

The SQMC 210 computes signal quality metrics. The SQMC 210 may receive various types of input, including: raw digitized Red and IR signals, a degree of arrhythmia, individual pulse quality, pulse amplitude variation, pre-processed Red and IR signals, and/or average pulse period. The SQMC 210 may output lowpass and ensemble averaging filter weights, normalized pre-processed waveforms, and/or percent modulation. These signal quality metrics may then be utilized in accordance with present embodiments to set parameters for other processes.

As set forth above, the PIQS 202 operates to qualify or reject potential pulses. In accordance with present embodiments, the PIQS 202 includes a counter 212 that keeps a record of consecutive rejected and qualified pulse counts. Specifically, when a pulse is qualified or rejected, the counter 212 updates counts of consecutive qualified or rejected pulses. Specifically, in one embodiment, the counter 212 sets a Reject_Count_High flag to a TRUE state once a designated number (e.g., 4) of pulses have been rejected and sets the Reject_Count_High flag to a FALSE state when a designated number (e.g., 3) of consecutive pulses have been qualified. Based on the state of the Reject_Count_High flag and other system variables (e.g., type of sensor), certain constants in algorithms utilized by the PIQS 202 may be adjusted, as will be discussed in detail below. For example, alternate constant values may be implemented when the state of the Reject_Count_High flag is TRUE. These bi-valued constants, as well as some other constants utilized in the PIQS 202, may include constants developed and tuned on large oximetry databases using genetic algorithms.

In accordance with present embodiments, the PIQS 202 may incorporate a state machine 214 that identifies maximum and minimum pulse phases. For example, the state machine 214 may identify a maximum phase when the current input sample value is less than the minimum of the previous N samples, and the state machine 214 is searching for a maximum phase. A minimum phase may be identified when the current input sample value is greater than the maximum of the previous N samples and the state machine 214 is searching for a minimum phase. It should be noted that the state machine 214 may be adapted to identify each phase at its final sample, not at the maxima or minima within that phase. Accordingly, the PIQS 202 may buffer the previous N samples of its input waveform, in addition to the current sample. Maximum and minimum phases may overlap. Several pulse parameters must be saved at the state transitions for use in qualifying the pulse. These parameters and their use are discussed in further detail below.

The state machine 214 may track regular pulses up to 300 BPM inclusive. In one embodiment, a designated sample interval, such as 17.5 msec, is utilized. To track 300 BPM pulses at a 17.5 msec sample interval, N is no greater than 60/(300*0.0175)=11.42=11 samples. If there are significant beat-to-beat variations in pulse amplitude, pulse period, and DC level, it has been observed that an N as low as 8 may be used to reliably track even 250 BPM pulses, particularly with arrhythmias.

In one embodiment, the value of N determines the shortest pulse that the state machine 214 can detect, and therefore acts as a time-based noise gate. If it is known that the pulse rate is substantially lower than 300 BPM, a larger value of N would be desirable in order to reduce the likelihood of high frequency interference being interpreted as pulses. Accordingly, in some embodiments, N is set based on the average pulse period for the PIQS 202, Avg_Period (the average pulse period), which is provided by the PRCS 204:

$$N = \text{bound}((int)(0.33*\text{Avg\_Period}), 8, 12) \tag{1}$$

where the notation bound(a, b, c) means min(max(a, b), c). This equation assures that N=8 when Avg_Period<=27 samples (=127 BPM), that N=12 when Avg_Period>=37 (=93 BPM), and varies linearly within this range. If Avg_Period=0 (no average period calculated yet), N is calculated using the previous potential pulse period instead. N defaults to 8 on the first potential pulse because there is no previous potential pulse period. As would be appreciated by one of ordinary skill in the art, different constant values may be implemented to obtain different desired results.

A waveform that has been highpass filtered may have a minimum phase that is much shorter than its maximum phase. Its duration can also vary due to physiological factors other than the pulse rate. Some adult patients have occasional pulses where the minimum phase lasts less than 12 samples (e.g., 210 msec), but that otherwise appear normal. To assure that the subsystem detects and then qualifies such pulses when they are definitely too large to be noise, a minimum phase may be identified when the current input sample value is greater than the maximum of the first M of the previous N samples. M is normally equal to N, but may be limited to 8 samples if both of the following conditions are met:

1) (Current Sample-Value 7 Samples Ago)>2*Gated_RMS, wherein Gated_RMS is the primary variable used to compute a noisegate for the PIQS 202.

2) The percentage of rejected pulses is less than 32%. This condition assures that the value of M will not be reduced during periods of sustained interference.

Detecting a potential minimum when the current sample exceeds the maximum of the earliest M of N samples, rather than the latest M samples, helps to assure that pulses that would be detected without this exception are still detected on the same sample. This, in turn, prevents this exception from adding an extra source of variability to the pulse periods. To minimize the number of comparisons required when searching the N-sample window, the subsystem starts comparing the current sample to the earliest, rather than the latest, sample.

Detecting maximum and minimum phases using a moving window excludes phases that are shorter than M or N samples. The state machine 214 may fail to detect pulses at rates significantly greater than 250 BPM. In the aberrant case of a divergent highpass-filtered waveform, the state machine 214 could theoretically identify a new phase each sample, detecting pulse with periods as short as two samples (e.g., 1710 BPM at a sample rate of 17.5 msec). Such output would be rejected by the pulse qualification criteria discussed below.

Data from certain types of sensors, such as head sensors, may include overly strong harmonics due to other influences, such as the influence of venous pulsation, which would be particularly emphasized in the highpass-filtered waveform. Accordingly, when a head sensor is in use, the subsystem lowpass filters its pulse identification waveform, to assure proper identification of physiologic pulse periods despite strong harmonics. A filter equation in accordance with present embodiments is as follows:

$$\text{Pulse\_Identification\_Waveform}_t = \text{Pulse\_Identification\_Waveform}_{t-1} + \text{Head\_Sensor\_LP\_Filter\_Weight} * (\text{IR\_Input\_Waveform}_t - \text{Pulse\_Identification\_Waveform}_{t-1}) \quad (2)$$

Equations for setting Head_Sensor_LP_Weight will be discussed below with respect to low-pass filter coefficients.

When a non-head sensor is in use and no pulses have been qualified yet, the PIQS 202 may perform minimal lowpass filtering to reduce noise susceptibility:

$$\text{Pulse\_Identification\_Waveform}_t = \text{Pulse\_Identification\_Waveform}_{t-1} + \max(0.5, 1.0 - \text{Unadjusted\_RoR\_Variance}) * (\text{IR\_Input\_Waveform}_t - \text{Pulse\_Identification\_Waveform}_{t-1}) \quad (3)$$

The Unadjusted_RoR_Variance metric is described in further detail below with respect to metrics for pulse qualification.

Some conditions may cause the state machine 214 to identify multiple potential pulses within each physiologic pulse. For example, interference may cause a single pulse to appear as though it includes multiple potential pulses. However, the PIQS 202 includes criteria for identifying and ignoring these extra potential pulses that occur due to noise or dicrotic notches. The PIQS 202 may compare these criteria with observed data when the minimum phase of each potential pulse is identified. In one embodiment, when a potential pulse is ignored, the period of the pulse will keep incrementing instead of being reset to zero.

The criteria for detecting noise and dicrotic notches introduce several variables, including the following:

1) Baseline=Average of input samples, computed with an IIR filter. The Baseline variable is used to compute Expected_Min_2 and Noise_Gate.

2) Curr_Sample=IR Pulse_Identification_Waveform$_t$ at the end of the minimum phase.

3) Expected_Min_1=An expected pulse minima relative to the value of Curr_Sample.

4) Expected_Min_2=An expected pulse minima relative to both Curr_Sample and Baseline.

5) Expected_Min_3=A floor on expected pulse minima, based on the value of Baseline.

6) Expected_Min=A value between Expected_Min_1 and Expected_Min_2, depending on the value of Frequency_Ratio, but not less than Expected_Min_3.

7) Frequency_Ratio=A characterization of the frequency content of the plethysmograph relative to the pulse rate. For example, a sine wave at a designated pulse-rate estimate may have a Frequency_Ratio of 1.0, while a sine wave at twice the pulse-rate estimate would have a Frequency_Ratio of 2.0.

8) Potential_Pulse_Min=The minimum of the previous N samples at the end of the minimum phase.

9) Last_Potential_Pulse_Min=Potential_Pulse_Min for the previous potential pulse.

10) Potential_Pulse_Period=The number of samples in a potential pulse.

11) Potential_Pulse_Period=A variable that is incremented every sample and reset to zero after each potential pulse.

12) Potential_Pulse_Sum=The sum of all samples in a potential pulse. Potential_Pulse_Sum is updated every sample and reset to zero after calculating Potential_Pulse_Avg.

13) Potential_Pulse_Avg=Potential_Pulse_Sum/Potential_Pulse_Period.

14) Last_Potential_Pulse_Avg=Potential_Pulse_Avg for the previous potential pulse.

15) Avg_Potential_Pulse_Avg=(Potential_Pulse_Avg+Last_Potential_Pulse_Avg)/2.

16) Noise_Gate=A threshold based on the amplitude of the "pulse" or "potential pulse." The rules for setting Noise_Gate are defined later in this document.

17) Notch_Flag=A flag that identifies whether a potential pulse is small enough to be a dicrotic notch.

18) Notch_Percent=The percentage of recent potential pulses for which Notch_Flag is set.

19) Pulse_Period=The current pulse period, in samples. Pulse_Period is incremented every sample and reset to zero after the pulse qualification criteria are applied.

20) Potential_Pulse_Path_Ratio=Potential_Pulse_Path_Length/(Potential_Pulse_Pulse_Max−Potential_Pulse_Pulse_Min), where Potential_Pulse_Path_Length=$\sum$|current sample−previous sample| for all samples in the potential pulse. This ratio is normally close to 2.0 in the absence of high-frequency noise.

21) Potential_Pulse_Alt_Path_Ratio=max((Potential_Pulse_Path_Length+final sample of previous potential pulse−final sample of current potential pulse)/(Potential_Pulse_Max−Potential_Pulse_Pulse_Min), 2).

By way of example, in a highpass-filtered waveform, local minima may occur in the middle of each pulse. However, these "potential pulses" may have an amplitude substantially smaller than the real pulse amplitude, the minimum may be above the baseline, and/or the rise time after the real pulse minimum may be relatively short. If the physiologic pulses were regular, they would be more readily distinguished from high-frequency interference by requiring the minima to be below Baseline. However, this approach could cause real pulses to be missed in cases of arrhythmia or irregular pulse amplitude. In such cases, it would be desirable to detect noise by looking at the rise of the waveform in the samples after the local minima. In accordance with present embodiments, the PIQS 202 gradually shifts its noise detection from the latter to the former approach as Frequency_Ratio increases (e.g., an increase from 1.25 to 1.85), while assuring that potential pulses that go well below baseline will not be ignored if their rise after the minimum is slow. A Frequency_Ratio value of 1.25 is typical of normal pulses after processing by SCS 206, while a Frequency_Ratio value of 1.85 is characteristic of normal pulses with high frequency interference that is not quite large enough to prevent a human from visually identifying the pulses.

Short-term high-frequency artifacts have been observed to be particularly common in surgical cases. Therefore, PIQS 202 also shifts towards requiring the minimum to be below Baseline as the Pulse_Period becomes significantly shorter than Avg_Period, particularly with little or no arrhythmia as quantified by the Period_Var metric, which relates to variability of the Pulse_Period. The equations for these criteria are as follows:

1) Ignore pulses if Potential_Pulse_Min>Expected_Min,
2) Expected_Min=max(Expected_Min_3, w*Expected_Min_2+(1−w)*Expected_Min_1),
3) Expected_Min_1=Current_Sample−Noise_Gate,
4) Expected_Min_2=min(Current_Sample−Noise_Gate, Baseline−0.5*Noise_Gate),
5) Expected_Min_3=Baseline−2*Noise_Gate,
6) w=(max(Frequency_Ratio, (Avg_Period/Pulse_Period−Period_Var))−1.25)/0.60, w=bound(w, 0, 1).

If the minimum phase is symmetric about Potential_Pulse_Min, then Curr_Sample should occur roughly 4 to 6 samples after Potential_Pulse_Min, depending on the value of N.

In some cases, strong dicrotic notches could have amplitudes larger than the noise gate. However, dicrotic notches can be clearly distinguished by a human because the waveform alternates between large and small "potential pulses." With a highpass-filtered waveform, the distance between the minima and the pulse average is typically much smaller for the dicrotic notch than for the entire pulse.

The rules for identifying and ignoring dicrotic notches in accordance with present exemplary embodiments are as follows:

Notch_Flag is TRUE if the following two criteria are met, otherwise Notch_Flag is FALSE:

1) The Dicrotic Notch Detection Neural Net outputs a value that exceeds a threshold. In one embodiment, this threshold is 0.5. The Dicrotic Notch Detection Neural Net will be discussed in more detail below.

2) (Curr_Sample−Potential_Pulse_Min)>0.5*Noise_Gate The second criterion for setting Notch_Flag is intended to keep noise from increasing the value of Notch_Percent, while still allowing fairly small dicrotic notches to be recognized. The equation for updating Notch_Percent on every potential pulse is:

if Notch_Flag is TRUE, $\text{Notch\_Percent}_t = \text{Notch\_Percent}_{t-1} + 0.04*(100-\text{Notch\_Percent}_{t-1})$ if Notch_Flag is FALSE, $\text{Notch\_Percent}_t = \text{Notch\_Percent}_{t-1} - 0.04*\text{Notch\_Percent}_{t-1}$.

To prevent underflow, the second update equation may be skipped if Notch_Percent is very close to zero (≤0.01). Potential pulses are ignored if Notch_Flag is TRUE and Notch_Percent>Notch_Percent_Thresh. It should be noted that Notch_Percent_Thresh is the threshold value, which is a weighting factor relating to characterizing pulse shapes. In one embodiment, Notch_Percent_Thresh has a value of 33 and in other embodiments (e.g., embodiments implementing a head sensor), Notch_Percent_Thresh is not used. Additionally, in some embodiments values other than 33 may be set for the threshold depending on desired results. In accordance with present embodiments, the value of Notch_Percent_Thresh may be automatically alternated based on certain conditions (e.g., performance data). Specifically, if Reject_Count_High is TRUE and/or certain other criteria are met (e.g., a head sensor is not in use), an alternative Notch_Percent_Thresh is used. For example, a value of 24 may be used instead of 33 for Notch_Percent_Thresh. This alternate value modestly increases the likelihood that the dicrotic notch check will keep interference from being misidentified as a pulse.

The response time and threshold for Notch_Percent are intended to allow dicrotic notches to be ignored in a timely manner once they appear, without causing real pulses to be ignored due to arrhythmia or intermittent interference. When dicrotic notches are present, Notch_Percent should have a value near 50. If a patient suddenly develops dicrotic notches, Notch_Percent will take about 13 pulses (26 potential pulses) to increase from zero to a threshold of 33. Notch_Percent may start to increase while the notches are small enough to still fail the Noise_Gate check. If dicrotic notches are not ignored, they will typically be disqualified by the pulse qualification criteria shown below, and be misclassified as artifact.

Figure 3:
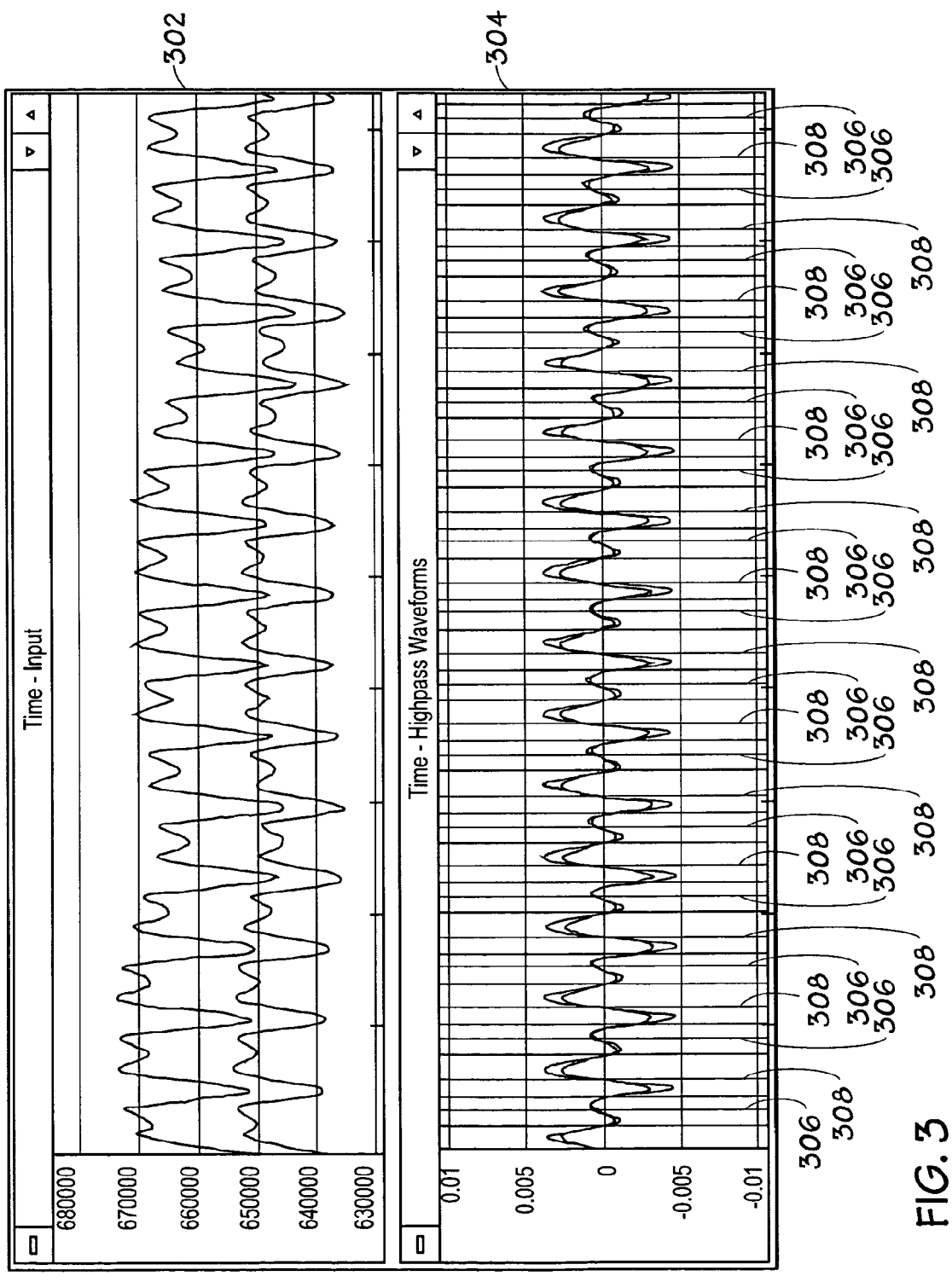
FIG. 3 is a graph illustrating ADC samples and a highpass filtered waveform that has been interpreted in accordance with an exemplary embodiment of the present invention.

FIG. 3 is a graph illustrating ADC samples and a highpass filtered waveform that has been interpreted in accordance with embodiments of the present invention. Specifically, FIG. 3 shows dicrotic notches being successfully ignored by the PIQS 202. A top window 302 shows ADC values, and a bottom window 304 shows the highpass-filtered waveform. The vertical lines 306 indicate potential pulses that were identified as dicrotic notches and ignored. The lines 308 indicate accepted pulse minima.

Figure 4:
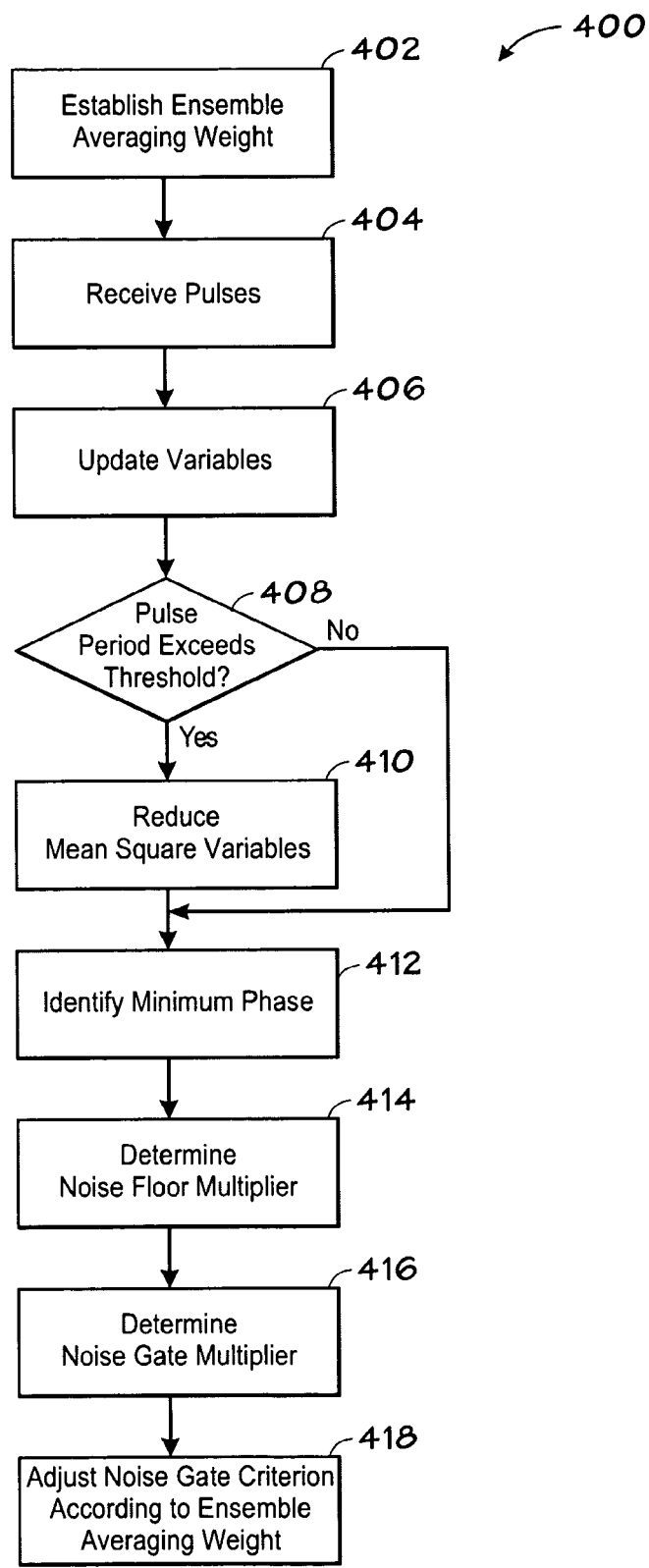
FIG. 4 is a flowchart illustrating a method for adjusting a noise gate parameter of a noise gate in relation to an ensemble averaging weight in accordance with an exemplary embodiment of the present invention.

FIG. 4 is a flowchart illustrating a method for adjusting a noise gate parameter of a noise gate in relation to an ensemble averaging weight in accordance with embodiments of the present invention. The method is designated by reference number 400. Ensemble averaging filtering may reduce noise levels, which may allow for a lowered noise gate. Accordingly, the ensemble averaging weight, which indicates the degree of ensemble averaging, may be used to adjust the noise gate parameter.

The method 400 begins at block 402, which represents establishing an ensemble averaging weight. An ensemble averaging weight may refer to a weight value that is used to calculate a weighted average of new samples and previously ensemble averaged samples from a previous pulse period. Any suitable ensemble averaging weight may be used. In one embodiment, Ensemble_Averaging_Weight is the ensemble-averaging weight used to compute the subsystem's input waveform by the Ensemble Averaging subsystem, if applicable. If the input waveforms are not ensemble-averaged, the value of Ensemble_Averaging_Weight will be 1.0, while a value of Ensemble_Averaging_Weight near zero would indicate a high degree of ensemble-averaging.

Pulses are received at block 404. Variables describing the pulses are updated at block 406. The variables may be updated in any suitable manner. For example, the variables may be updated for each sample, prior to the every-potential-pulse, according to the following operations:

1. Baseline represents an average of input samples and may be updated according to the following equation:

$$\text{Baseline}_t = \text{Baseline}_{t-1} + c_1 \Delta t * (\text{Curr\_Sample} - \text{Baseline}_{t-1}) \quad (4)$$

where $c_1$ represents a constant, $\Delta t$ is the sample interval in seconds, and t is in samples. In one embodiment, $c_1$ has a value of 0.5. This formula gives Baseline a two-second response time. Constant $c_1$ may be any suitable value, such as $c_1 = 1.0$ for a one-second response time, given sampling interval $\Delta t = 10$ msecs.

2. Mean_Square represents the mean-square of input samples. Mean_Square may be computed with an IIR filter and corrected for non-zero baselines, and may be updated according to the following equation:

$$\text{Mean\_Square}_t = \text{Mean\_Square}_{t-1} + k*((\text{Curr\_Sample} - \text{Baseline}_t)^2 - \text{Mean\_Square}_{t-1}) \quad (5)$$

where k represents a constant selected to yield a Means_Square with a particular response time. For example, k may be determined according to the following equation to yield a Mean_Square with a response time of one second or one pulse, whichever is shorter:

$$k = \max(1/\text{Avg\_Period}, \Delta t), \text{ if Avg\_Period} > 0;$$

$$k = \max(1/\text{Potential\_Pulse\_Period}, \Delta t), \text{ if Potential\_Pulse\_Period} > 0 \text{ AND the previous Potential\_Pulse\_Period is 0 AND Avg\_Period} = 0; \text{ and}$$

$$k = \Delta t, \text{ if Avg\_Period} = 0 \quad (6)$$

A short response time may allow Mean_Square to decline quickly when interference ends, to reduce the likelihood of real pulses being ignored. During the first potential pulse, for up to one second, the above formula gives equal weight to each sample, to prevent initial underestimates of Mean_Square$_t$ as it diverges from zero.

3. Gated_RMS represents the square root of Mean_Square used to compute Noise_Gate. Since negative input samples tend to represent the pulse, rather than noise, Gated_RMS may only be updated on input samples that exceed Baseline. Gated_RMS may be updated according to the following equation:

$$\text{Gated\_RMS}_t = \sqrt{\text{Mean\_Square}_t}, \text{ if Curr\_Sample} > \text{Baseline}_t.$$

$$\text{Gated\_RMS}_t = \text{Gated\_RMS}_{t-1}, \text{ if Curr\_Sample} \leq \text{Baseline}_t \quad (7)$$

At block 408, the pulse period may exceed a threshold that indicates that a pulse has just been missed or will occur shortly. The threshold may have any suitable value, such as two seconds. In one exemplary embodiment, once Pulse_Period exceeds two seconds, approximated as 114 samples, it is likely that the pulse has already been missed or will occur very shortly. If the pulse period exceeds the threshold at block 408, the method 400 proceeds to block 410. In block 410 mean square parameters such as Mean_Square and Gated_RMS are reduced as follows.

$$\text{Gated\_RMS}_t = (1-\Delta t)\text{Gated\_RMS}_t$$

$$\text{Mean\_Square}_t = (1-\Delta t)\text{Mean\_Square}_t \quad (8)$$

In the exemplary embodiment, the reductions would be performed on every sample where Pulse_Period>114. This operation is performed immediately after the updates for Mean_Square and Gated_RMS shown above.

After block 410, the method 400 proceeds to block 412. Additionally, if the pulse period does not exceed the threshold at block 408, the method 400 proceeds to block 412. The minimum phase of a potential pulse is identified at block 412. The minimum phase may be identified when the value of Curr_Sample$_t$ has a specified relationship to previous or subsequent Curr_Sample values. For example, a minimum phase may be identified when Curr_Sample$_t$ exceeds samples that occurred in the previous 100 to 150 msecs. Blocks 414-418 describe updating the noise gate parameter of a noise gate criterion. A noise gate criterion may refer to a parameter that controls the threshold that identifies whether a waveform includes noise. For example, the noise gate parameter may be adjusted to reduce the noise gate level if the ensemble averaging weight indicates an increased degree of ensemble averaging.

According to one embodiment, the noise gate parameter Noise_Gate may be defined according to the following equation:

$$\text{Noise\_Gate} = \max(n*\text{Gated\_RMS}, (c_2 + c_3 * \text{EAW})*m*\text{Noise\_Floor}/\text{IR\_DC}) \quad (9)$$

where n represents the noise gate multiplier, EAW represents Ensemble_Averaging_Weight, m represents a noise floor multiplier, IR_DC represents the current infrared (IR) A/D values, and Noise_Floor represents a minimum noise level associated with the oximetry hardware, which determines a minimum value for the noise gate, and $c_2$ and $c_3$ represent any suitable constants. In one embodiment $c_2$ and $c_3$ each have a value of 0.5.

The noise floor multiplier of the noise gate parameter is set at step 414. The noise floor multiplier may be set in any suitable manner. As an example, noise floor multiplier m may initially be set to a unit value (e.g., m=1.0). Subsequent values of m may be set according to the following equation:

if $|\text{Avg\_Period} - \text{Pulse\_Period}| < c_5*\text{Avg\_Period}$ $$m = 1 - c_4*(c_5*\text{Avg\_Period} - |\text{Avg\_Period} - \text{Pulse\_Period}|)/(c_5*\text{Avg\_Period})$$

else if $|\text{Avg\_Period} - \text{Potential\_Pulse\_Period}| < c_5*\text{Avg\_Period}$ $$m = 1 - c_4*(c_5*\text{Avg\_Period} - |\text{Avg\_Period} - \text{Potential\_Pulse\_Period}|)/(c_5*\text{Avg\_Period})$$

else if $\text{Potential\_Pulse\_Period} < c_6*\text{Avg\_Period}$ $$m = 1 + (c_4*l)/(c_5*\text{Avg\_Period}) \quad (10)$$

where Pulse_Period represents the pulse period of the current pulse, l represents a parameter, and $c_4$, $c_5$, and $c_6$ represent constants having any suitable value. For example, in one embodiment $c_4$ has a value of 0.5, $c_5$ has a value of 0.25, and $c_6$ has a value of 0.75.

Parameter l may be determined by the following equation:

$$l = w((1-c_5)*\text{Avg\_Period} - \text{Potential\_Pulse\_Period}) + (1-w)*(c_5*\text{Avg\_Period} - \min(|c_4*\text{Avg\_Period} - \text{Potential\_Pulse\_Period}|, c_5*\text{Avg\_Period}))$$

where $$w = (\text{Frequency\_Ratio} - c_7)/c_8$$

$$w = \max(0, \min(1, w)) \quad (11)$$

and where Frequency_Ratio represents the frequency content of plethysmograph relative to the pulse rate, and $c_7$ and $c_8$ represent constants having any suitable values. For example, in one embodiment, $c_7$ has a value of 1.25 and $c_8$ has a value of 0.6.

According to one embodiment, if Avg_Period is zero, then m is calculated using the previous Potential_Pulse_Period in place of Avg_Period, provided that the previous Potential_Pulse_Period is acceptable for modifying m. For example, the duration of the previous Potential_Pulse_Period may be required to satisfy a threshold indicating that the pulse periods are less likely to reflect noise (e.g., Potential_Pulse_Period may be required to corresponds to a rate that is slower than about 150 BPM where "slower than 150 BPM" is implemented as "≥23 samples," or 402.5 msec at a 17.5 msec sample rate). This function may be represented by the following formula:

$$\text{If Avg\_Period}=0, \text{Mean\_Square}_f=\max(\text{Mean\_Square}_p, c_9*\text{Potential\_Pulse\_Amp}^2) \quad (12)$$

where Potential_Pulse_Amp represents the amplitude of a pulse, and $c_9$ represents a constant having any suitable value (e.g, a value of 0.12). Potential_Pulse_Amp may be given as Potential_Pulse_Amp=Potential_Pulse_Max−Potential_Pulse_Min, where Potential_Pulse_Max represents the maximum of the previous N samples at the end of the maximum phase preceding the minimum phase, and Potential_Pulse_Min represents the minimum of the previous N samples at the end of the minimum phase. This formula is intended to set Mean_Square, and consequently Noise_Gate, high enough to prevent noise from being treated as pulses after initialization.

The noise gate multiplier n is established at block 416. The noise gate multiplier n may be established in any suitable manner. According to one embodiment, n may be established according to the following equation:

if Pulse_Period>Potential_Pulse_Period $n=c_{10}*m*\text{bound}(c_{11}+\text{Potential\_Pulse\_Skew},c_{12},c_{13})$ else if Skew_Derivative_Input_Weight>$c_{14}$ $n=c_{10}*m*\text{bound}(c_{15}+\text{Potential\_Pulse\_Skew},c_{12},c_{13})$ else $n=c_{10}*m$. \quad (13)

where Skew_Derivative_Input_Weight represents a weight used to combine the Curr_Sample waveform with its derivative to obtain a waveform having a more negative skew, Potential_Pulse_Skew represents the skewness of the samples in this combined waveform over the duration of the Potential_Pulse_Period, and $c_{10}$, $c_{11}$, $c_{12}$, $c_{13}$, $c_{14}$, and $c_{15}$ represent constants having any suitable values (e.g., $c_{10}$=0.85, $c_{11}$=1.5, $c_{12}$=0.4, $c_{13}$=1.0, $c_{14}$=8.0, and $c_{15}$=2.0).

As set forth above, Potential_Pulse_Skew represents the skewness of the potential pulse. The equation for skewness is:

$$\frac{n\sum (x_i - \bar{x})^3}{(n-1)(n-2)\sigma^3} \quad (14)$$

where x is the waveform from which the skewness metric is computed, σ is the standard deviation of x, and n is the number of samples in the potential pulse. For Potential_Pulse_Skew, x is the Curr_Sample. Normalizing by σ makes this metric scale-independent. The equation for σ is:

$$\sigma = \sqrt{\frac{n(\sum x_i^2) - (\sum x_i)^2}{n(n-1)}} = \sqrt{\frac{\sum (x_i - \bar{x})^2}{(n-1)}} \quad (15)$$

where the summations are computed over the n samples in the potential pulse. In order to compute and subtract $\bar{x}$, x must be buffered for the duration of the potential pulse. In accordance with some embodiments, since pulses longer than 172 samples may be rejected by certain qualification criterion, n and the buffer length for x may be limited to 172 samples. If n is less than a designated value (e.g., 3), or if the expression under the square root sign is not positive, the skew metric may be set to zero. In order to compute a non-zero skew, the input waveform, x, must include harmonics of the pulse rate.

In accordance with embodiments of the present invention, under certain designated conditions, alternative values are applied to constants in the equations above. Specifically, constants or terms in the equations set forth above may be automatically replaced with an alternate value or one of several alternate values based on system performance and system attributes. For example, in one embodiment, if Reject_Count_High is TRUE and a head sensor is not in use, two of the constants may be changed as follows:
1) The multiplier $c_{10}$ in the equations for n may be switched from a value of 0.85 to a value of 1.03,
2) The $c_4$*Avg_Period term in the equation for 1 may be switched from 0.5*Avg_Period to 0.584*Avg_Period.

These alternate values affect modest increases in the noise gate during periods of interference, particularly for Potential_Pulse_Periods between approximately 54% and 75% of Avg_Period.

Block 418 represents adjusting the noise gate parameter according to the noise floor multiplier and the noise gate multiplier. After updating the noise gate parameter, the method 400 may end. However, it should be noted that modifications, additions, or omissions may be made to the method 400 without departing from the scope of the invention.

The period-dependent noisegate adjustments discussed above help to reduce the likelihood of real pulses being ignored, particularly those that are not highly skewed, while improving the likelihood of dicrotic notches and high-frequency interference being ignored. The first skew-based adjustment reduces the likelihood of ignoring more than one real pulse immediately after transient interference. In some embodiments a derivative is used. Because a derivative goes up slower than it goes down, this skew-based adjustment reduces the likelihood that the shallow rise of the derivative will be treated as noise. The skew-based adjustment that occurs when Skew_Derivative_Input_Weight>$c_{14}$ may apply when the waveform used to compute the Skew metric gives a high positive weight to the derivative of curr_sample. This has been observed to occur almost exclusively with head sensors.

During monitoring, if a patient's heart happens to skip a beat on the first qualified pulse, or if the first qualified pulse is actually an artifact near half the true heart rate, then subsequent pulse periods would consistently be near half of the resultant initial value of Avg_Period. This would increase the value of m, and make it more difficult to update Avg_Period, potentially causing the pulse rate to get "stuck" at half the correct value. Accordingly, in accordance with some embodiments, the pulse period used to scale m is "phased in" over the first several (e.g., 5) qualified. For example, in one embodiment, the following equation is utilized:

$x$=22 if Potential_Pulse_Amp>0.0005, otherwise
$x$=24 if Potential_Pulse_Period$_{t-1}$≥x AND Total_Qualified_
Pulses<5

Noise_Gate_Scaling_Period=w*Avg_Period+(1−w)*
Potential_Pulse_Period$_{t-1}$ else, Noise_Gate_Scaling_Period=Avg_Period  (16)

where w represents Total_Qualified_Pulses/5, and Total_Qualified represents the total number of pulses qualified since subsystem reinitialization. In one embodiment, Total_Qualified need not be incremented beyond 100 and, therefore, may be explicitly limited to 100 to prevent integer overflow.

This reduces the influence that a single qualified pulse period can have on noise gate scaling for future pulses, so that these can be properly detected, and qualified, and allows the PRCS 204 algorithm pulse-rate estimate to converge quickly if it does start out too low. Varying a "150 BPM" threshold slightly based on Potential_Pulse_Amp has been found empirically to improve pulse identification. A 0.0005 threshold for Potential_Pulse_Amp corresponds to a raw IR modulation of about 0.2%.

If a potential pulse is smaller than the Noise Floor, it is concatenated into the next potential pulse in accordance with present embodiments. This reduces the likelihood of breaking up pulses with amplitudes close to the Noise Floor into multiple "potential pulses" that could drive the pulse-rate estimate too high. In the event that some real pulses with amplitudes smaller than the Noise Floor are concatenated with the next pulse, these concatenated pulses will have very high Path_Ratio metrics that get them disqualified. This will generally keep pulses with marginal signal-to-noise ratios from driving the pulse-rate estimate too low. Specifically, the following exceptions are made if a potential pulse fails the Noise_Gate test when Noise_Gate is equal to m*Noise_Floor:

1) The Last_Potential_Pulse_Min, Last_Potential_Pulse_Avg, the previous Potential_Pulse_Period, and the final sample of the previous potential pulse used to
    calculate Potential_Pulse_Alt Path_Ratio, are not updated.
2) Potential_Pulse_Period, Potential_Pulse_Sum and Potential_Pulse_Path_Length are not reset to zero.

However, if |Noise_Gate_Scaling_Period−Pulse_Period|<c$_{16}$*Noise_Gate_Scaling_Period, where c$_{16}$ is any suitable constant (e.g., 0.25), these exceptions will not be made in accordance with present embodiments, as this exception to the exception has been found empirically to reduce initial rate errors in the presence of hardware noise.

The equation for Noise_Floor assumes that the oximeter's noise floor contains a component that is independent of IR gain (ADC noise, etc.), and another component that is proportional to the oximeter's gain (I-V converter noise, etc.):

$$\text{Noise\_Floor} = \sqrt{(m*\text{IR\_Gain})^2 + b^2} \quad (17)$$

where IR_Gain is the product of the oximeter's variable gains in the IR channel, and the constants m and b depend on the hardware platform and the frequency response of the derivative waveform. It should be noted that the PIQS 202 may set all noise-floor estimates at startup and whenever IR_Gain or Red_Gain changes. IR and Red noise-floor estimates must be divided by IR_DC or Red_DC because the subsystem's input waveforms have been normalized by the DC level. IR_DC and Red_DC represent current IR and Red ADC values.

In accordance with present embodiments, the PIQS 202 may use a neural net to determine whether a potential pulse is a dicrotic notch. In one embodiment, it outputs a value between 0.0 and 1.0, where values above 0.50 indicate a dicrotic notch. In one embodiment, the neural net is trained in Matlab using the Levenberg-Marquardt back propagation method. Such a training algorithm may be responsible for finding and optimizing the relationships between the neural net's inputs and its desired output. The neural net can be retrained if desired. Retraining and recharacterization of the neural net is a well-defined, semi-automated process. In one embodiment, the trained neural net is implemented as an array of dot products and a few transcendental functions. Retraining may only require an update to the neural net's coefficients, leaving the code unchanged. In one embodiment, the neural net may be trained, optimized and evaluated on large databases containing a wide range of patients and conditions, including arrhythmia, noise, motion, and respiratory artifact.

A human can reliably identify dicrotic notches by looking at the relative amplitudes and periods of consecutive potential pulses. In ambiguous cases, a human may be able to look at additional data, such as ECG, to make a determination. In general, dicrotic notches are substantially smaller than the pulse amplitude, are sustained over periods of many pulses, have a fixed phase relationship to the pulse, and substantially increase the energy at the second harmonic of the heart rate. Some arrhythmias also involve alternating large and small pulses, but most of the energy is still near the average pulse rate, instead of at half the pulse rate. Respiratory artifact may occur at close to half the pulse rate, but does not tend to stay in-phase with the pulse.

For every potential pulse, the PIQS 202 may compute the following four inputs for its Dicrotic Notch Detection Neural Net in accordance with present embodiments:

METRIC 1—quantifies the relative depth of the current and previous potential pulse minima:

$$\text{Metric1} = \ln(\max(\min(x,100)0.01)) \quad (18)$$

$$x = \frac{\text{Avg\_Potential\_Pulse\_Avg} - \text{Potential\_Pulse\_Min}}{\text{Avg\_Potential\_Pulse\_Avg} - \text{Last\_Potential\_Pulse\_Min}}$$

Metric1 = ln(100), if Avg_Potential_Pulse_Avg ≤ Last_Potential_Pulse_Min

The clipping, and log scaling all help to limit the input range over which the neural net must be trained. Avg_Potential_Pulse_Avg is used to compute Metric 1 because it represents a baseline value for the entire pulse, whether dicrotic notches are present or not. The default value of ln(100) is the limit of Metric 1 as Last_Potential_Pulse_Min converges toward Avg_Potential_Pulse_Avg without exceeding it.

METRIC 2—quantifies the relative period of the potential pulse:

$$\text{Metric2} = \ln(\max(\min(\text{Potential\_Pulse\_Period}/\text{Avg\_Period},1.5),0.4)) \quad (19)$$

Metric 2 is set to zero if the average pulse period, Avg_Period, is still zero. The default value of zero is what Metric 2 would be if all potential pulse periods were identical. The clipping helps to limit the input range over which the neural net must be trained.

METRIC 3—is the value of Metric 1 from 2 potential pulses ago. If enough potential pulses have not occurred yet, Metric 3 is set to zero, which is what it would be if all potential pulse minima were identical.

METRIC 4—is the value of Metric 1 from 3 potential pulses ago. If enough potential pulses have not occurred yet, Metric 4 is set to zero, which is what it would be if all potential pulse minima were identical.

In accordance with one embodiment, the neural net is a feed-forward network with a six-node hidden layer and a single-node output layer. All nodes are fully connected, and have associated bias inputs. The hidden layer therefore contains (4+1)*6=30 tunable coefficients, and the output layer contains (6+1)*1=7 tunable coefficients. These coefficients may be specific both to the types of oximetry data that were used to train the neural net and to the particular processing that occurs in earlier parts of the algorithm, such as blocks 206 and 208.

The jth neuron in a layer has n inputs, $x_{1 \ldots n}$, n weights, $w_{1,j \ldots n,j}$, a bias, $b_j$, a transfer function F( ) and an output, $y_j$:

$$y_j = F\left(b_j + \sum_{i=1}^{n} w_{i,j} x_i\right) \quad (20)$$

All nodes in a layer receive the same inputs, although they have different weights and biases. The inputs to the hidden layer are the four input metrics described above. The inputs to the output layer are the outputs of the four hidden nodes in the hidden layer.

Because the neural net's training goal is to output a weight between 0 and 1, the output node and all hidden nodes use the logarithmic sigmoid, or logsig( ), transfer function, which compresses an infinite signed input range into an output range of 0-1. The formula for the logsig( )transfer function is:

$$\log \text{sig}(x) = (1+e^{-x})^{-1} \quad (21)$$

In order to prevent the exponential in this equation from over or underflowing, x should be constrained to appropriate limits. Limiting x to +/−64 is sufficient to prevent over or underflow with an 8-bit floating-point exponent. Limiting x to +/−11 provides sufficient resolution for a 16.16 fixed-point representation.

To qualify pulses reliably during interference, as well as during clinical situations such as arrhythmia, dicrotic notches, etc., it is desirable for pulse qualification software to take a variety of principles into account such as:

a) The heart takes less time to pump blood into the arteries than the arteries take to squeeze it back out through the capillaries. This gives the derivative of the plethysmograph a negative skew. At normal heart rates, the ejection time of the human heart is about 200 msec.
b) This skewness is less pronounced for shorter pulse periods, and varies between patients.
c) Real pulses have consistent pulse periods, unless the patient is arrhythmic.
d) In many arrhythmic patients, pulse period and pulse amplitude are highly correlated with each other.
e) Very young patients, whose pulses are short and not very skewed, almost never have arrhythmias.
f) The normal plethysmograph goes up and down once per pulse, or has a small dicrotic notch in the middle.
g) Dicrotic notches tend to be of consistent amplitude relative to the pulse.
h) Interference tends to have a more symmetric shape than a pulse.
i) When low-amplitude high-frequency interference is simultaneous with adult pulses, the pulse can often be visually identified, due to its greater amplitude.
j) Human arterial pulses exhibit low variability in the IR/Red Ratio-of-Ratios, while interference exhibits more Ratio-of-Ratios variability.
k) Respiratory artifacts, particularly from ventilated patients, are usually at lower frequencies than the pulse rate. Often the pulse can be visually identified, although the Ratio-of-Ratios may be more variable, to the extent that the respiratory artifact reflects movement of non-arterial substances.
l) Interference may be many times larger than the real pulse, and may come and go instantly, whereas human pulses are usually of consistent amplitude.

The PIQS 202 qualifies pulses using neural nets whose input metrics and training enable them to quantify all of the above properties, based on combinations of multiple metrics. The inputs metrics exclude any absolute representation of pulse period or rate, so that the neural net will continue to qualify pulses during arrhythmia or other large pulse-rate changes. Three neural nets, as represented by reference numbers 216, 218, and 220, may be used in accordance with present embodiments:

1) The "Pulse Characterization" neural net 216 classifies pulses based only on properties of the current and three previous pulses. The output of the Pulse Characterization net 216 is used to update variable weights for filters that are intended to quantify the long-term properties of the patient's typical pulses, such as the degree of arrhythmia.

2) The "Pulse Qualification" neural net 218 receives these long-term input metrics as well as the pulse-to-pulse metrics seen by the Pulse Characterization net 216, so that its output is optimized for the patient and therefore more reliable.

3) A second instance of the Pulse Qualification neural net 220 receives input metrics from the most recent "good" pulses, instead of just the most recent pulses. This instance is less readily confused by prolonged interference, and more reliably qualifies good pulses during brief periods without interference, but is less likely to qualify pulses after rapid physiological changes.

The output of both Pulse Qualification nets 218 and 220 is fed into a feedback layer, which provides an output between zero (bad) and one (good) to the Pulse Qualification criteria. The second Pulse Qualification net 220 also uses this output to identify the recent "good" pulses for its input metrics.

In one embodiment, these neural nets are fully-connected feed-forward nets with a single hidden layer and logarithmic sigmoid transfer functions in both layers. In one embodiment, the Pulse Characterization net 216 has 12 inputs and 10 hidden nodes, and the Pulse Qualification nets 218 and 220 have 17 inputs and 10 hidden nodes. In one embodiment, the Pulse Characterization net 216 and the first instance of the Pulse Qualification net 218 have been trained and evaluated using clinical databases containing over 300,000 manually classified pulses representing a wide range of physiological and artifactual conditions, and the feedback layer has been tuned empirically.

The following variables must be introduced in order to define the neural nets' inputs:

$$\text{Unadjusted\_RoR\_Variance} = \sqrt{\frac{\sum_{i=0}^{M-1} (Red_{t-i} - IR_{t-i}R)^2}{\sum_{i=0}^{M-1} Red_{t-i}^2}}, \quad (22)$$

where $R = \dfrac{\sum_{i=0}^{M-1} IR_{t-i} Red_{t-i}}{\sum_{i=0}^{M-1} IR_{t-i}^2}$ Adjusted_RoR_Variance =

$$\sqrt{\dfrac{\sum_{i=0}^{M-1}\left((Red_{t-i} - IR_{t-i}R)^2 - \left(\left(\dfrac{Red\_Noise\_Foor}{Red\_DC_t}\right)^2 + R^2\left(\dfrac{IR\_Noise\_Foor}{IR\_DC_t}\right)^2\right)\right)}{\sum_{i=0}^{M-1} Red_{t-i}^2}},$$

where $R = \dfrac{\sum_{i=0}^{M-1} IR_{t-i} Red_{t-i}}{\sum_{i=0}^{M-1} IR_{t-i}^2}$ M=171 samples=3 seconds.

IR_Noise_Floor=⅓ of the Noise_Floor used to calculate Noise_Gate.

Red_Noise_Floor=⅔ of the Noise_Floor value that would be calculated using the gain of the Red channel instead of the IR channel. Noise-floor estimates may be lower than those used to calculate Noise_Gate because Noise_Gate is set to ignore peak-to-peak noise and Adjusted_RoR_Variance is an RMS noise estimate. The IR and Red inputs to the RoR_Variance metrics may be the outputs of SCS 206 or EAS 208, minus their mean values for M samples. The RoR_Variance metrics may be set to zero if either the numerator or denominator under the square-root sign is not positive, or if R is zero. If fewer than three seconds worth of samples are available, then M may be set to the number of available samples and the RoR_Variance metrics may be calculated using only those samples.

Pulse_Max=the maximum sample in the pulse-detection waveform during the pulse to be qualified.

Pulse_Min=the minimum sample in the pulse-detection waveform during the pulse to be qualified. A "pulse" may include all samples from the end of the minimum phase of the previous pulse to the end of the minimum phase of the current pulse, including any intervening "potential pulses" that were ignored. A "pulse" may be subsequently qualified or rejected by the pulse qualification criteria. Pulse_Max and Pulse_Min are updated every sample and reset to Curr_Sample after the pulse qualification criteria are applied, in preparation for the next pulse.

Pulse_Amp=Pulse_Max−Pulse_Min.

Path_Ratio=Path_Length/(Pulse_Max−Pulse_Min), where Path_Length=$\sum$|current sample−previous sample| for all samples in the pulse. This ratio is normally close to 2.0, and may reach about 3.0 if a dicrotic notch is present.

Alt_Path_Ratio=max((Path_Length+final sample of previous pulse−final sample of current pulse)/(Pulse_Max−Pulse_Min), 2).

Alt_Skew=The skewness of Curr_Sample over the entire Pulse_Period.

Skew=The skewness of x=Curr_Sample$_t$+w*(Curr_Sample$_t$−Curr_Sample$_{t-1}$) over the entire Pulse_Period. This combination may be adjusted every pulse to minimize Skew as follows:

w, shown as Skew_Derivative_Input_Weight in the Data Dictionary in Appendix A, defaults to 2.0. Each time a pulse is qualified, Skew is computed for the entire pulse period using w and using (w+1). If the computation using (w+1) produces a more negative Skew than the computation using w, then w is increased by n/1000, otherwise it is decreased by n/1000. For adult pulses, w typically has a value near 4 at a 17.5 msec sample interval. Abnormal physiologic pulse shapes may adjust w to negative values. To assure that a subsequent rapid resumption of normal pulse shapes does not prevent pulses from being qualified, and w from readjusting, the PIQS 202 may impose an empirically determined lower limit of −4.0 on the value of w.

High-frequency interference can sometimes drive Noise_Gate up so high that one or more valid pulses occurring right after the artifact fail the noise-gate check and are concatenated together with the artifact. This could cause the entire sequence of "potential pulses" (artifact+pulse) to be submitted as one "pulse" for qualification, and then rejected. In order to qualify more of these missed pulses, the final potential pulse may be submitted for Pulse Qualification instead of the entire "pulse," provided that its period is closer to the average qualified pulse period and its shape and size look better. Specifically, the final potential pulse may be required to meet all of the following criteria to be submitted for pulse qualification:

a) Pulse_Period>Potential_Pulse_Period (i.e. at least one potential pulse was already ignored)

b) Avg_Period>0 c) Pulse_Period*Potential_Pulse_Period>Avg_Period$^2$ (i.e. potential period is closer to average qualified period)

d) Skew−Potential_Pulse_Skew+Path_Ratio−Potential_Pulse_Path_Ratio+|ln(Pulse_Amp)−Avg_Ln_Pulse_Amp|−|ln(Potential_Pulse_Amp)−Avg_Ln_Pulse_Amp|>0.5 e) Notch_Flag was FALSE for the previous potential pulse.

Evaluating these criteria and submitting the final potential pulse for pulse qualification may include computing several new terms over those samples corresponding to the final potential pulse, including Potential_Pulse_Path_Length, Potential_Pulse_Path_Ratio, Potential_Pulse_Alt_Path_Ratio, and Potential_Pulse_Alt_Skew. The meanings of these variables are clear based on the definitions set forth above. If the potential pulse is submitted, then Potential_Pulse_Period, Potential_Pulse_Max, Potential_Pulse_Min, and Potential_Pulse_Sum will be used instead of Pulse_Period, Pulse_Max, Pulse_Min, and Pulse_Sum in the pulse qualification criteria and rate update equations below.

Ensemble-averaging tends to attenuate harmonics of the pulse more than the fundamental, resulting in slightly smaller pulses and a more sinusoidal pulse shape. This may cause the instance of the PIQS 202 that receives ensemble-averaged waveforms to qualify fewer pulses if the pulses are already very small and/or near-sinusoidal. In one embodiment, to compensate for this effect, Skew, Alt_Skew, and Pulse_Amp are adjusted at this point, prior to pulse qualification. Exemplary equations are as follows:

Skew=Skew−0.3*x

Alt_Skew=Alt_Skew−0.3*x

Pulse_Amp=(1+0.5*x)*Pulse_Amp   (23)

where x=(1.0−min(Ensemble_Averaging_Weight$_t$, Ensemble_Averaging_Weight$_{t-1}$))/0.9)$^2$ and the t−1 subscript denotes one pulse ago.

Figure 5:
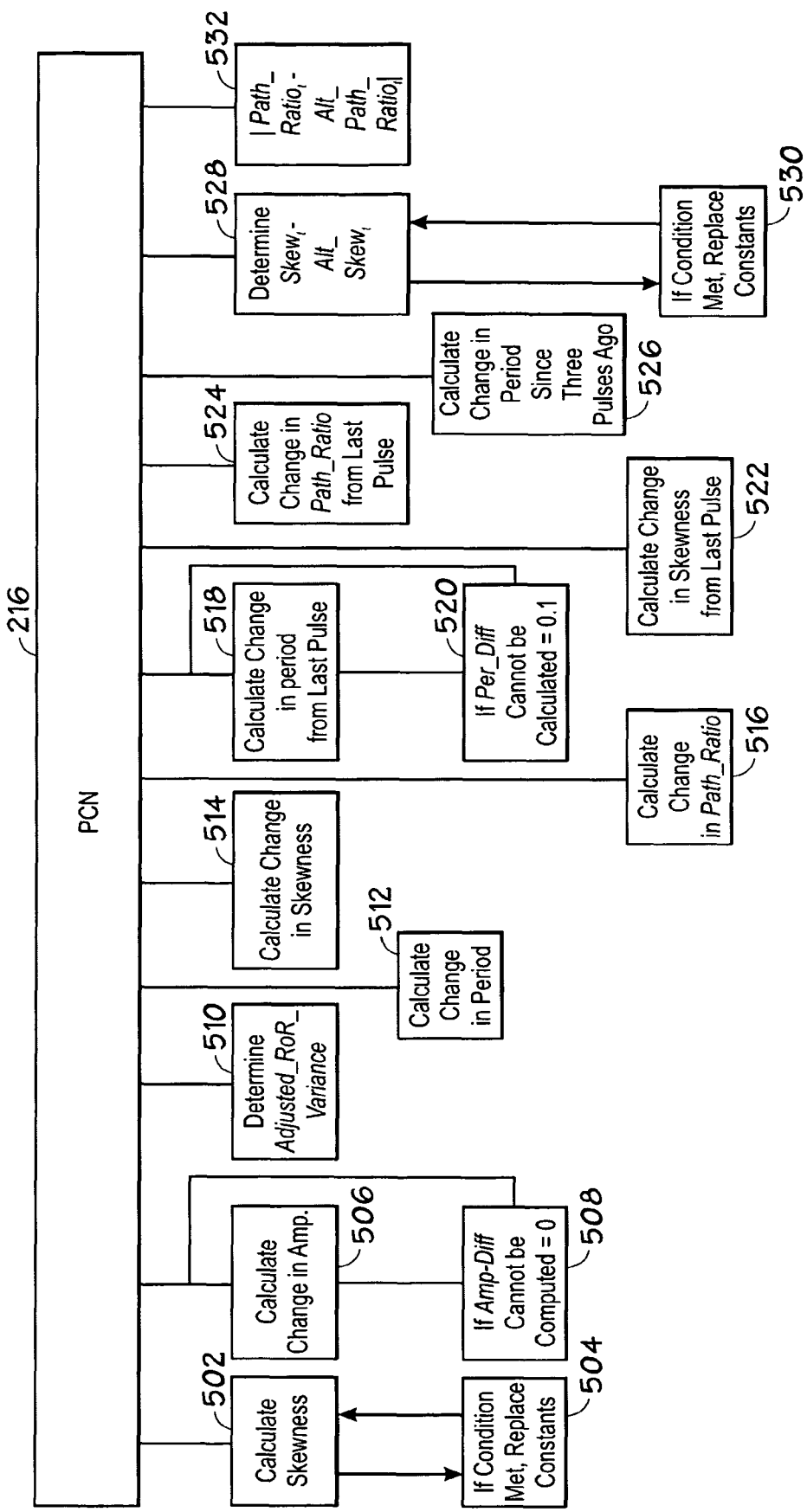
FIG. 5 is a block diagram of a method for providing the Pulse Characterization net with inputs in accordance with an exemplary embodiment of the present invention.

FIG. 5 is a block diagram of a method for providing the Pulse Characterization net 216 with inputs in accordance with embodiments of the present invention. It should be noted that in one embodiment, an Ensemble_Averaging_Weight of 1.0 indicates no ensemble-averaging, while a weight of 0.1 indicates a high degree of ensemble-averaging. For the instance of the PIQS 202 that receives waveforms that are not ensemble-averaged, Ensemble_Averaging_Weight is 1.0, in which case these adjustments will have no impact on that instance's metrics. Providing inputs to the Pulse Characterization net 216 may include the following:

1) As illustrated by block 502, the skewness of the pulse may be computed from an adjustable combination of its first and second derivatives with further adjustments for pulse period as follows: Adjusted_Skew$_t$=Skew$_t$+0.0181*(min(80, Pulse_Period$_t$)−40). This equation provides a roughly pulse-rate-neutral measure of pulse shape. Real pulses should have more negative values of this metric than artifact.

It should be noted that while different constants may be utilized, the exemplary embodiment uses specific values. The skew slope of 0.0181/sample was calculated for 13 adults whose heart rates ranged from 40 to 120 BPM. The 80-sample limit on the adjustment for Pulse_Period in the above equation corresponds to 1.4 seconds, or about 43 BPM. In one embodiment, as illustrated by block 504, these constants are automatically replaced with alternate constants when certain conditions are met. For example, if Reject_Count_High is TRUE or a head sensor is in use, an alternative value of 0.0151 per sample may be used to compute Adjusted_Skew instead of the value of 0.0181 shown above. For head sensors, the alternate value provides a more appropriate period-based adjustment for the less-skewed pulse shapes typical of these sites. For non-head sensors, the alternate value reduces the likelihood of misqualifying high-frequency interference as a pulse. As will be appreciated by one of ordinary skill in the art, different constant and alternative constant values may be utilized for different results, as well as different criteria for applying the alternative constant value to different constant and alternative constant values.

2) As illustrated by block 506, change in amplitude from the previous pulse may be calculated as follows: Amp_Diff$_t$=ln(Pulse_Amp$_t$/Pulse_Amp$_{t-1}$). Real pulses should have small values of this metric, or negative values if preceded by artifact. If Amp_Diff cannot be computed yet, it defaults to 0.10, as illustrated by block 508.

3) As illustrated by block 510, Adjusted_RoR_Variance may be determined. As specified above, this metric quantifies ratio-of-ratios variability (typically due to artifact), with adjustments for the noise floor contribution of the hardware. This metric ranges between zero and one. Real pulses should have lower values of this metric than artifact.

4) A change in period between one and two pulses ago, Per_Diff$_{t-1}$, may be calculated as illustrated by block 512 (see metric 6 below).

5) A change in skewness between one and two pulses ago, Skew_Diff$_{t-1}$ may be calculated as illustrated by block 514 (see metric 7 below).

6) A change in Path_Ratio metric between one and two pulses ago, Path_Diff$_{t-1}$, may be calculated as illustrated by block 516 (see metric 8 below).

7) As illustrated in block 518, change in period from last pulse may be calculated as follows: Per_Diff$_t$=ln(Pulse_Period$_t$/Pulse_Period$_{t-1}$). Values will be small for real pulses unless there is an arrhythmia. If Per_Diff cannot be computed yet, it defaults to 0.1, as illustrated by block 520.

8) Change in skewness from last pulse may be calculated in block 522 as follows: Skew_Diff$_t$=Adjusted_Skew$_t$−Adjusted_Skew$_{t-1}$. Values should have negative correlation with the previous metric during arrhythmia.

9) Change in Path_Ratio metric from last pulse may be calculated in block 524, as follows: Path_Diff$_t$=Path_Ratio$_t$−Path_Ratio$_{t-1}$. Values should be small for real pulses.

10) Change in period since three pulses ago may be calculated in block 526, as follows: Per_Diff$_t$=ln(Pulse_Period$_t$/Pulse_Period$_{t-3}$).

11) Skew$_t$−Alt_Skew$_t$ may be determined in block 528. This metric will usually be negative for real pulses. Evaluation of surgical data gathered with a forehead sensor has revealed that the neural nets as presently trained have difficulty qualifying pulses with large negative values of this metric in combination with arrhythmia. Therefore, in one embodiment, this metric is multiplied by (1.05−Period_Var), provided Alt_Skew$_t$>Skew$_t$, Period_Var>0.05, and pulses have already been qualified. This rescaling allows the neural net to perceive the pulse as having a slightly more "arterial" pulse shape. Other constants may be used in accordance with present embodiments to achieve different results. Further, in one embodiment, constants used in this rescaling may be automatically replaced when certain conditions are met, as illustrated by block 530. For example, in one embodiment, if Reject_Count_High is TRUE and a head sensor is not in use, the Period_Var-based rescaling uses alternative values of 1.10 and 0.10 instead of 1.05 and 0.05, as interference may tend to increase Period_Var even without physiologic arrhythmia.

12) Path_Ratio$_t$−Alt_Path_Ratio$_t$| may be determined at block 532. Large values of this metric mean that the starting samples of consecutive pulses were very different, which is often indicative of arrhythmia.

In one embodiment, the Pulse Characterization neural net's output, Pulse_Char_Output, is only calculated if 11 samples≤Pulse_Period$_t$≤172 samples AND Pulse_Period$_{t-1}$ is available. If these preconditions are not met, its output may be set to zero, although the neural net's inputs are updated in anticipation of the next pulse. The Pulse Qualification neural nets, as well as their inputs, may only be updated when 11 samples<=Pulse_Period$_t$<=172 samples AND Pulse_Period$_{t-1}$ is available.

In accordance with present embodiments, for the first instance of the Pulse Qualification net 218, metrics 0-8 and 10 are identical to those of the Pulse Characterization net 216. Pulse Qualification metric 9 is identical, except that the value used for Pulse_Period$_{t-3}$ is held for up to two pulses when Pulse_Char_Output$_{t-3}$<0.5. This refinement to metric 9 increases the likelihood that this metric represents the difference in period between the current pulse and a previous good pulse. The t subscript here denotes all pulses, including the ones for which Pulse Characterization neural net's output was not calculated. While 0.5 is used as a constant, one of ordinary skill in the art would recognize that other values may be used to obtain different results. Further, in one embodiment if certain conditions are met, the constant is automatically replaced with an alternate value. For example, in one embodiment, if Reject_Count_High is TRUE and a head sensor is not in use, an alternative threshold of 0.06 may be applied instead of the threshold of 0.5 shown above.

The output of the Pulse Characterization net, Pulse_Char_Output, is used to determine a variable weight, w, used to update the Pulse Qualification neural net's long-term pulse history metrics:

$$w = \text{Pulse\_Char\_Output}_{t-1} * \text{Pulse\_Char\_Output}_{t-2}/N, \quad (24)$$

where N=1.0 for the first two pulses, and is then incremented by 1.0 for each pulse processed by the Pulse Characterization net 216 until it reaches 50. Because Pulse_Char_Output varies between zero (bad pulses) and 1.0 (good pulses), Pulse Qualification metrics that are filtered with this variable weight, w, will mostly reflect the characteristics of the good pulses, and will change much more slowly for "pulses" that are really artifact. The t subscript in the formula for w, and in the equations below, denotes only those pulses for which Pulse Characterization neural net's output was calculated.

Figure 6:
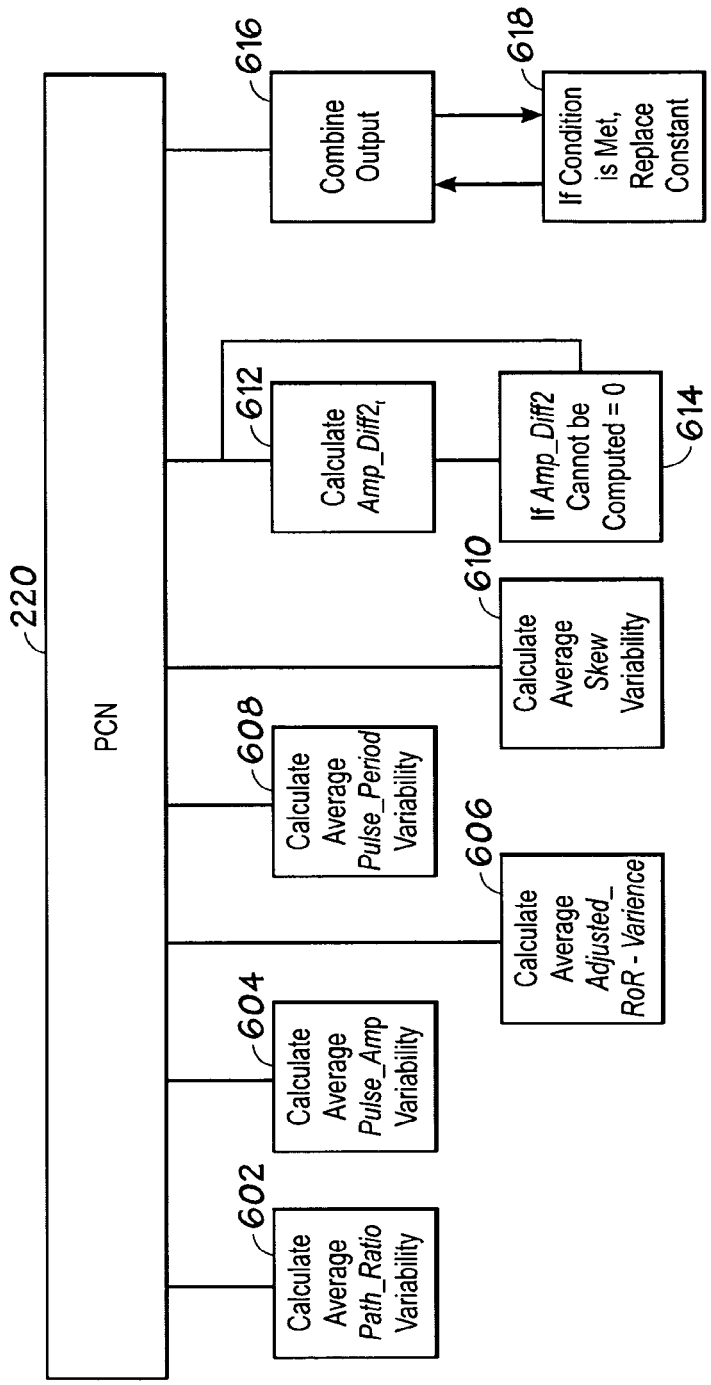
FIG. 6 is a block diagram of a method for determining Pulse Qualification net inputs that represent long-term history in accordance with an exemplary embodiment of the present invention.

FIG. 6 is a block diagram of a method for determining Pulse Qualification net inputs that represent long-term history in accordance with embodiments of the present invention. In this method, most of the Pulse Qualification neural net's inputs may be reused from the Pulse Characterization neural net. Indeed, the inputs from blocks 502-528 are inputs to block 220. However, it should be noted that the inputs for block 532 are not inputs to block 220. Providing these inputs may include the following acts:

12 Average Path_Ratio variability may be calculated in block 602 as follows: $\text{Path\_Ratio\_Var}_t = (1-w)*\text{Path\_Ratio\_Var}_{t-1} + w*|\text{Path\_Diff}_{t-1}|$. Note that this input replaces the final input in the Pulse Characterization net 216.

13) Average Pulse_Amp variability may be calculated in block 604 as follows: $\text{Amp\_Var}_t = (1-w)*\text{Amp\_Var}_{t-1} + w*|\text{Amp\_Diff}_{t-1}|$. This input, as well as metrics 14) and 15) below, helps the neural net to adjust to arrhythmic patients.

14) Average Adjusted_RoR_Variance may be calculated in block 606 as follows: $\text{RoR\_Variance\_Avg}_t = (1-w)*\text{RoR\_Variance\_Avg}_{t-1} + w*\text{Adjusted\_RoR\_Variance}_{t-1}$. This input helps the neural net to adjust to patients with respiratory (ventilator) artifact.

15) Average Pulse_Period variability may be calculated in block 608 as follows: $\text{Period\_Var}_t = (1-w)*\text{Period\_Var}_{t-1} + w*|\text{Per\_Diff}_{t-1}|$.

16) Average Skew variability may be calculated in block 610 as follows: $\text{Skew\_Var}_t = (1-w)*\text{Skew\_Var}_{t-1} + w*|\text{Skew\_Diff}_{t-1}|$.

17) Amp_Diff2$_t$ may be calculated in block 612, as follows: $\text{Amp\_Diff2}_t = \ln(\text{Pulse\_Amp}_t)/\text{Avg\_Ln\_Pulse\_Amp}_t$, where $\text{Avg\_Ln\_Pulse\_Amp}_t = (1-w)*\text{Avg\_Ln\_Pulse\_Amp}_{t-1} + w*\ln(\text{Pulse\_Amp}_{t-1})$. This input improves detection of artifacts that are much larger than the patient's normal pulse amplitude. If Amp_Diff2 cannot be computed yet, it defaults to zero, as illustrated by block 614.

Very large sudden increases in pulse amplitude could cause subsequent pulses to be disqualified until Avg_Ln_Pulse_Amp catches up. Therefore, if N is at least a set number of pulses (e.g., 25), Avg_Ln_Pulse_Amp may be updated with a faster response in the presence of pulses that produce consistently high Pulse Characterization neural net output as follows:

$$\text{Avg\_Ln\_Pulse\_Amp}_t = (1-w2)*\text{Avg\_Ln\_Pulse\_Amp}_{t-1} + w2*\ln(\text{Pulse\_Amp}_{t-1}).$$

$$w2 = w*\text{bound}(x, 1.0, 4.0)$$

$$x = \min(\text{Pulse\_Char\_Input}_t, \text{Pulse\_Char\_Input}_{t-1})/2 \quad (25)$$

where Pulse_Char_Input is the input to the logsig( )transfer function at the output node of the Pulse Characterization neural net 216. These long-term history metrics may be completely independent of the current pulse, so that the current pulse does not bias the history metrics in order to qualify itself.

On occasion, extremely large changes can occur in the characteristics of two consecutive "pulses." For instance, a several-second asystole might create a very large Per_Diff value, and a large transient interference might create a very large Amp_Diff value. To prevent such rare anomalies from biasing the long-term history metrics, single-step increases in the Path_Ratio_Var, Amp_Var, Period_Var, and Skew_Var metrics may be limited to a maximum (e.g., 0.05 per "pulse").

The second instance of the Pulse Qualification 220 net differs only in the pulses used to provide short-term pulse history metrics 1 and 3-9. The t−1, t−2, and t−3 subscripts in the equations for these metrics no longer denote the most recent pulses, but rather the three most recent "good" pulses, where "good" means $\text{Dual\_Pulse\_Qual\_Output}_t > c_1$ AND $\text{Pct\_Rejected} < c_2$, where $c_1$ and $c_2$ may be 0.8636 and 0.45, respectively. An output threshold of 0.8636 indicates a very high probability that the qualified pulse was physiologic. A Pct_Rejected threshold of 0.45 means that nearly half of recent pulses were qualified for pulse-rate calculation. Implementing a history of only "good" pulses may include saving the Pulse_Period, Adjusted_Skew, Pulse_Amp, and Path_Ratio each time a "good" pulse occurs.

As illustrated by block 616, the output of the dual instances of the Pulse Qualification net 218 and 220 is combined at the feedback layer as follows:

$$\text{Dual\_Pulse\_Qual\_Output}_t = \text{logsig}(\max(x1_t - c_{17}, x2_t) + c_{18}*\text{Avg\_Pulse\_Qual\_Output}_{t-1} - c_{19})$$

$$\text{Avg\_Pulse\_Qual\_Output}_t = \min(c_{20}, c_{21}*\text{Dual\_Pulse\_Qual\_Output}_t + c_{22}*\text{Avg\_Pulse\_Qual\_Output}_{t-1}) \quad (26)$$

where x1 is the input to the first Pulse Qualification net's logarithmic sigmoid transfer function at its output node, x2 is the corresponding input of the second Pulse Qualification net 220, whose inputs are only from "good" pulses, and $c_{17}$, $c_{18}$, $c_{19}$, $c_{20}$, $c_{21}$, and $c_{22}$ are suitable constants (e.g., $c_{17}=0.2$, $c_{18}=3$, $c_{19}=1.18$, $c_{20}=0.50$, $c_{21}=0.08$, and $c_{22}=0.92$). In one embodiment, the constants may be replaced with alternate constants if certain conditions exist, as illustrated by block 618. For example, in one embodiment, if Reject_Count_High is TRUE and a head sensor is not in use, then Avg_Pulse_Qual_Output$_t$ is computed using an alternative value of 0.06 for $c_{20}$ instead of the threshold of 0.5.

Combining of the outputs from the two nets improves the likelihood of qualifying a pulse that looks like either previous good pulses or very recent pulses, without biasing the output too high. The feedback equation then penalizes its output for previous bad outputs, to decrease the likelihood of qualifying artifactual "pulses" during periods of prolonged uninterrupted artifact.

Figure 7:
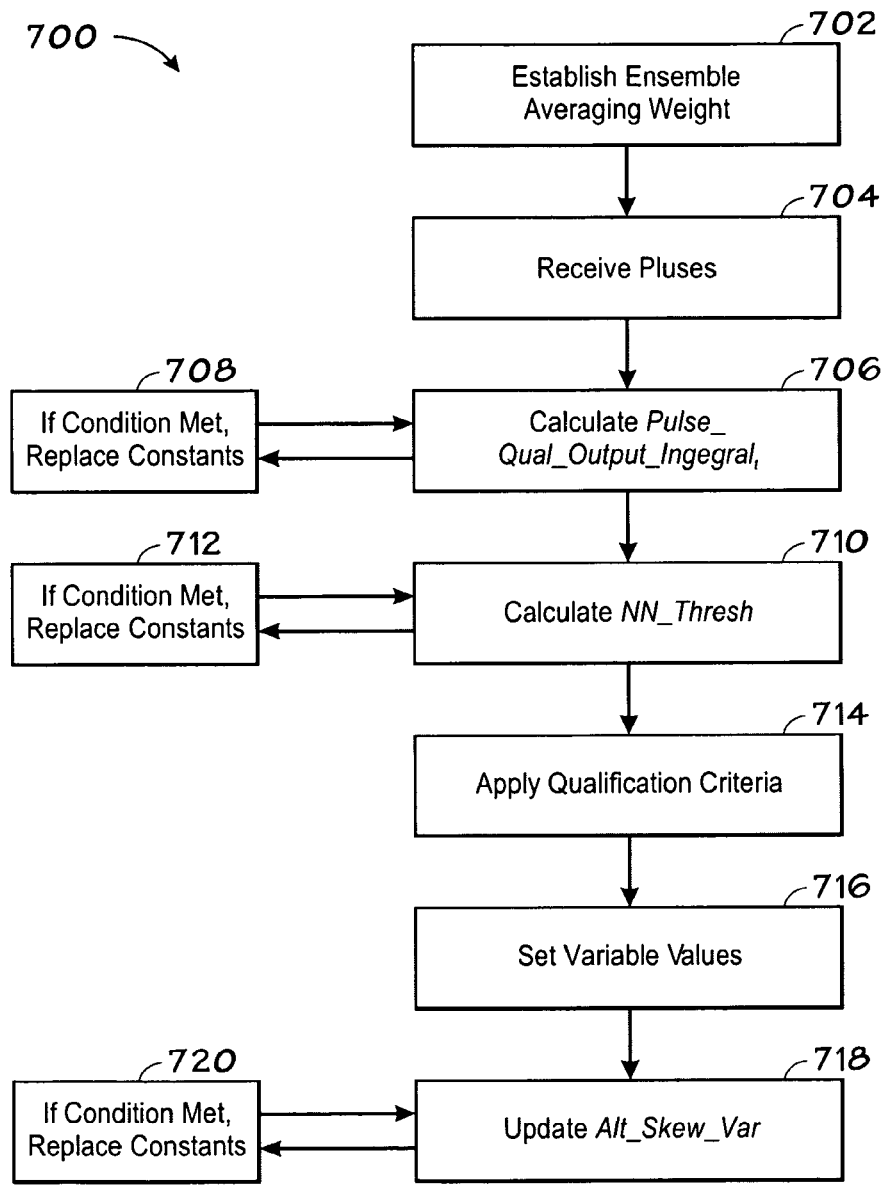
FIG. 7 is a flowchart illustrating adjusting a pulse period criterion in agreement with an ensemble averaging weight in accordance with an exemplary embodiment of the present invention.

FIG. 7 is a flowchart illustrating adjusting a pulse period criterion in agreement with an ensemble averaging weight in accordance with embodiments of the present invention. The method is generally designated by reference number 700. In the illustrated embodiment, an ensemble averaging weight may indicate that a qualified pulse is not likely to have a pulse period that is substantially shorter than an average pulse period.

The method 700 begins at block 702, which represents establishing an ensemble averaging weight. Pulses are received at block 704. Additional blocks, as set forth below, describe evaluating the received pulses in accordance with pulse qualification criteria. The pulse qualification criteria may be applied in any suitable order. According to one embodiment, the pulse qualification criteria are applied in the order set forth herein, and if a pulse fails in one criterion, subsequent criteria are not applied In one embodiment, the pulse qualification criteria are applied to each pulse, which includes a non-ignored potential pulse plus zero or more previously ignored potential pulses. The criteria introduce the following variables: NN_Thresh, Pulse_Qual_Output_Integral$_t$, Initial_Pulse_Count, Last_Pulse_Period, Pulse_Sum, Pulse_Avg, Last_Pulse_Min, Avg_Min. The Initial_Pulse_Count may be set equal to the number of non-ignored pulses found since the subsystem was reinitialized. Further, Initial_Pulse_Count may be incremented after the pulse qualification criteria are evaluated. For certain pulse qualification criteria in accordance with present embodiments, Initial_Pulse_Count does not need to exceed 100, and therefore may be explicitly limited to 100 to prevent integer overflow. The Last_Pulse_Period variable represents the Pulse_Period for the previous non-ignored pulse. The Pulse_Sum variable represents the sum of all samples in a pulse. Pulse_Sum may be updated every sample and reset to zero after calculating Pulse_Avg. The Pulse_Avg variable may be defined as Pulse_Sum/Pulse_Period. The Last_Pulse_Min variable represents Pulse_Min for the previous pulse. The Avg_Min variable may be defined as (Last_Pulse_Min+Pulse_Min)/2. The variables NN_Thresh and Pulse_Qual_Output_Integral$_t$ are discussed in detail below.

Block 706 represents calculation of the Pulse_Qual_Output_Integral$_t$ in accordance with present embodiments. The Pulse_Qual_Output_Integral$_t$ may be defined by the following equation:

$$\text{Pulse\_Qual\_Output\_Integral}_t = \min(\text{Pulse\_Qual\_Output\_Integral}_{t-1} + \text{Dual\_Pulse\_Qual\_Output}_t - c_{23}, c_{24})$$

if Dual_Pulse_Qual_Output$_t \le c_{25}$

Pulse_Qual_Output_Integral$_t$=0 where $c_{23}$, $c_{24}$, and $c_{25}$ represent any suitable value (e.g., $c_{23}$=0.5, $c_{24}$=100, and $c_{25}$=0.5). In accordance with present embodiments, alternative thresholds may be utilized when certain conditions are met, as illustrated by block 708. For example, in one embodiment, if Reject_Count_High is TRUE and other conditions are met (e.g., a head sensor is not in use), an alternative threshold may be applied (e.g., instead of the threshold of 0.5 shown above, 0.06 may be applied). This improves the subsystem's ability to continue to qualify pulses during periods of interference.

Block 710 represents calculation of NN_Thresh in accordance with present embodiments. In one embodiment, NN_Thresh may be given by the following equation:

$$NN\_\text{Thresh} = c_{26} + c_{27}*(\text{Period\_Ratio} - c_{28});$$

$NN$_Thresh=$c_{29}$, if Avg_Period is zero (no pulses qualified yet)

where Period_Ratio represents the ratio of the current period and the average period, and $c_{26}$, $c_{27}$, $c_{28}$, and $c_{29}$ represent constants having any suitable values (e.g., $c_{26}$=0.4, $c_{27}$=0.25, $c_{28}$=1.0, and $c_{29}$=0.5). Period_Ratio may be given by the following equation:

$$\text{Period\_Ratio} = \min(2, \max(\text{Pulse\_Period/Avg\_Period}, \text{Avg\_Period/Pulse\_Period})).$$

These equations may vary the neural-net output threshold for qualifying a pulse from 0.4 when the pulse period is equal to the subsystem's average qualified period to 0.65 when these differ by a factor of two or more. In accordance with present embodiments, alternative thresholds may be utilized when certain conditions are met, as illustrated by block 712. For example, if Reject_Count_High is TRUE and/or other conditions are met (e.g., a head sensor is not in use), alternative thresholds may be applied (e.g., instead of the thresholds of 0.4 and 0.5 shown above, thresholds of 0.03 and 0.06 may be applied). This improves the ability of the PIQS 202 to continue to qualify pulses during periods of interference.

Pulse qualification criteria comprising one or more criteria are applied at block 714. For example, pulses may be rejected when a pulse fails any of the following criteria:

1) Pulse_Min<Pulse_Avg<Pulse_Max. This test should rarely if ever fail.
2) Avg_Min<Pulse_Avg<Pulse_Max. This test fails if Last_Pulse_Min is much higher than Pulse_Avg, that is, if local blood volume changes cause a steep decline in the baseline.
3) 11 samples<=Pulse_Period<=172 samples. While other thresholds may be utilized in accordance with present embodiments, these thresholds correspond to 311.69 and 19.93 BPM respectively at a 17.5 msec sample rate, and are the closest approximations to 300 and 20 BPM.
4) Dual_Pulse_Qual_Output$_t$>NN_Thresh.
5) Pulse_Qual_Output_Integral$_t \ge 0.26$ if no pulses have been qualified yet. This threshold means that the initial estimate for Avg_Period will be due to either one very good pulse (>95% probability of being real) or multiple fairly-good pulses in succession.
6) |Pulse_Period–Last_Pulse_Period|≤0.1*Initial_Pulse_Count*Pulse_Period, and Initial_Pulse_Count>1. This test is intended to prevent inaccurate initial pulse estimates by requiring that consecutive pulse periods agree closely, and gradually relaxing this period agreement threshold with each successive pulse. The first pulse is rejected because there is no prior pulse period to compare it to.
7) Path_Ratio<4.0 if no pulses have been qualified yet. This reduces the likelihood of initializing the pulse-rate estimate to values that are too low under noisy conditions.
8) (Avg_Period–Pulse_Period)≤2*Avg_Period*min(Ensemble_Averaging_Weight$_t$, Ensemble_Averaging_Weight$_{t-1}$); if Avg_Period>0. This check disqualifies shorter-than-normal periods in ensemble-averaged waveforms that are presumably artifacts of incorrect ensemble averaging. Longer-than-normal periods may occur if the patient's heart skips a beat, and it is desirable to qualify these.

Block 716 represents setting variable values based on pulse qualifications. Specifically, the method 700 sets Qualified_Pulse_Period to Pulse_Period, and sets Pulse_Qualified and Beep_Now flags, on each pulse that passes all of the pulse qualification criteria. Qualified_Pulse_Period may then be made available to the PRCS 204, which may calculate Avg_Period and corresponding pulse rate. Further, method 700 sets a Pulse_Rejected flag on each non-qualified pulse and sets Qualified_Pulse_Period to zero. It also sets the Beep_Now flag on non-qualified pulses that meet all of the following requirements:

a) Criteria 1, 2, 4, 5, or 8 did not fail
b) Initial_Pulse_Count exceeds 1
c) |Avg_Period–Samples_Since_Beep|<0.1*Avg_Period AND
d) Avg_Period>500 msec AND
e) Samples_Since_Pulse_Qualified<2.5*Avg_Period.

These criteria allow up to two consecutive beeps on non-qualified pulses at adult pulse rates, provided the non-qualified pulse occurs very close to when the user anticipates the next beep. In one embodiment, as represented by block 716, the Artifact flag is set to TRUE whenever any of criteria 1, 2, 4, 5, or 8 fails, provided the Beep_Now flag is FALSE and Initial_Pulse_Count exceeds 1. It remains TRUE on the next pulse for which Beep_Now is set. It is set to FALSE on the second pulse for which Beep_Now is set.

In one embodiment, the Consecutive_Qualified count is incremented when a pulse is qualified and set to zero when it is rejected. The Consecutive_Rejected count is incremented when a pulse is rejected and set to zero when it is qualified.

The Reject_Count_High flag is set to TRUE if Consecutive_Rejected≥4 and is set to FALSE if Consecutive_Qualified≥3. Consecutive_Qualified and Consecutive_Rejected do not need to exceed 100, and are therefore explicitly limited to 100 to prevent integer overflow.

The subsystem updates Head_Sensor_LP_Filter_Weight each time it attempts to qualify a pulse. It has been observed that if extra high-frequency "wiggles" are added to the derivative of a normal human plethysmograph, the skewness of the individual "wiggles" is, on average, less negative than the skewness of the same waveform computed over a time interval that encompasses one or more pulses periods. Therefore, each time the subsystem computes its Alt_Skew metric for a "pulse period," it also computes a Fixed_Interval_Skew metric for the most recent two seconds of Curr_Sample. The subsystem then adjusts Head_Sensor_LP_Filter_Weight to assure that the value of Alt_Skew is not significantly less negative than the value of Fixed_Interval_Skew. This goal will only be achieved if the subsystem is using complete physiologic pulse periods to compute Alt_Skew.

Because the shape of consecutive high-frequency "wiggles" is much more variable than the shape of consecutive physiologic pulse periods, the PIQS 202 also quantifies the variability of Alt_Skew in its Alt_Skew_Var metric. In one embodiment, as illustrated in block 718, it updates Alt_Skew_Var after the Pulse Qualification neural net has evaluated each "pulse," using the following equations:

$$\text{Adjusted\_Alt\_Skew}_t = \text{Alt\_Skew}_t + c_{30} * (\min(c_{31}, \text{Pulse\_Period}_t) - c_{32})$$

$$w = \text{Dual\_Pulse\_Qual\_Output}_t / \max(N, 1)$$

$$\text{Alt\_Skew\_Var}_t = w * |\text{Adjusted\_Alt\_Skew}_t - \text{Adjusted\_Alt\_Skew}_{t-1}| + (1-w) * \text{Alt\_Skew\_Var}_{t-1} \quad (27)$$

where $c_{30}$, $c_{31}$, and $c_{32}$ are variables having any suitable values (e.g., $c_{30}=0.0181$, $c_{31}=80$, and $c_{32}=40$), $N=1.0$ for the first two pulses, and is then incremented by 1.0 for each pulse processed by the Pulse Characterization net 216 until it reaches as designated value (e.g., 50). The use of the pulse qualification neural net's output as a weight to filter Alt_Skew_Var allows it to discount "pulses" that the neural net disqualifies. The adjustment for Pulse_Period matches that done by the Pulse Qualification neural net 218, 220. Alt_Skew_Var values much above 0.3 are not characteristic of correctly identified physiologic pulses. Values of 0.5 to 0.9 are characteristic of misidentified fragmentary pulses. In some embodiments, constants may be replaced with alternate values if certain conditions are met, as illustrated by block 720. For example, if Reject_Count_High is TRUE or a head sensor is in use, an alternative value of 0.0151 per sample may be used to compute Adjusted_Alt_Skew instead of the value of 0.0181 shown above. For head sensors, the alternate value provides a more appropriate period-based adjustment for the less-skewed pulse shapes typical of these sites. For non-head sensors, the alternate value reduces the likelihood of misqualifying high-frequency interference as a pulse.

The equations for Head_Sensor_LP_Filter_Weight are as follows:

$$\text{Skew\_Delta} = \text{Fixed\_Interval\_Skew}_t + 0.0507 - \text{Alt\_Skew}_t$$

if Alt_Skew_Var>0.3, Skew_Delta=Skew_Delta*min(Alt_Skew_Var,0.8)/0.3

$$\text{Weight\_Multiplier} = 1 + 0.2005 \Delta t * \text{Pulse\_Period}_t * \text{Skew\_Delta}$$

$$\text{Head\_Sensor\_LP\_Filter\_Weight}_t = \text{Head\_Sensor\_LP\_Filter\_Weight}_{t-1} * \max(0.809, \text{Weight\_Multiplier})$$

$$\text{Head\_Sensor\_LP\_Filter\_Weight}_t = \text{bound}(\text{Head\_Sensor\_LP\_Filter\_Weight}, 0.1, 1.0)$$

$$\text{Pct\_Rejected\_Based\_Weight} = 0.531 - 0.8 * \text{Pct\_Rejected}_{t-1}$$

if Alt_Skew_Var>0.3,
Pct_Rejected_Based_Weight=Pct_Rejected_Based_Weight-Alt_Skew_Var-0.3)

$$\text{Head\_Sensor\_LP\_Filter\_Weight}_t = \max(\text{Head\_Sensor\_LP\_Filter\_Weight}_t, \text{Pct\_Rejected\_Based\_Weight})$$

where $\Delta t$ is the 0.0175 second sample interval. As would be understood by one of ordinary skill in the art, the constants used above may be changed for different desired results.

These equations were determined empirically based on analysis data from challenging surgical cases with mixed arterial and venous pulses that included strong harmonics. The minimum weight of 0.1 levels off the frequency response of the PIQS 202 highpass-filtered input waveforms at around 2 Hz. As Pct_Rejected decreases from approximately 0.5 to zero, the minimum weight also increases from 0.1 to approximately 0.5. A weight of approximately 0.5 levels off the frequency response of the PIQS 202 input waveforms at around 10 Hz. However, high values of Alt_Skew_Var mitigate the effect of low Pct_Rejected values, and accelerate the adjustment of Head_Sensor_LP_Filter_Weight.

The Pct_Rejected metric reflects the fraction of recent pulses that have been rejected. It is updated each time a pulse is qualified or rejected as follows:

On qualified pulses:

$$\text{Pct\_Rejected}_t = \text{Pct\_Rejected}_{t-1} - 0.1 * \text{Pct\_Rejected}_{t-1}$$

When a pulse is rejected because pulse qualification criterion 6) above failed:

$$\text{Pct\_Rejected}_t = \text{Pct\_Rejected}_{t-1}$$

Otherwise:

$$\text{Pct\_Rejected}_t = \text{Pct\_Rejected}_{t-1} + 0.1 * (1.0 - \text{Pct\_Rejected}_{t-1})$$

Pct_Rejected$_t$ is also updated if a potential pulse is "ignored" because it is smaller than the subsystem's noise gate AND the elapsed time since the previous non-ignored potential pulse exceeds the lesser of 172 samples or 2*Avg_Period (provided it is non-zero) AND more than 172 samples have elapsed since the last qualified pulse. This latter condition is intended to recognize that so much time has elapsed between non-ignored pulses that intervening pulses were missed. Head_Sensor_LP_Filter_Weight is also updated at this time, to assure that the lowpass filtering does not cause pulses to be continually missed. The update formulae for Pct_Rejected and Head_Sensor_LP_Filter_Weight at this time are:

$$\text{Pct\_Rejected}_t = \text{Pct\_Rejected}_{t-1} + 0.05 * (1.0 - \text{Pct\_Rejected}_{t-1})$$

Head_Sensor_LP_Filter_Weight$_t$=min $$(1.05 * \text{Head\_Sensor\_LP\_Filter\_Weight}_{t-1}, 1)$$

To prevent underflows, the first update equation for Pct_Rejected may be skipped if Pct_Rejected is very close to zero (≤0.00001), in which case Pct_Rejected may be explicitly set to zero.

Those skilled in the art will readily appreciate that it may be necessary to reinitialize the PIQS 202 in response to various events, for example when a sensor is applied to a new patient. The initial values of the various events in the PIQS 202 are specified in the Data Dictionary in Appendix A. Appendix A specifies non-zero default values for several variables related to the Pulse Qualification neural nets that are selected so as not to strongly dispose the neural nets to either accept or reject a pulse. Those skilled in the art will also recognize that, depending on the embodiment of the oximetry hardware, there may be brief periods when the subsystem cannot be updated with valid data from the SCS 206 or EAS 208, and that selected variables may need to be reset, updated, or left unchanged during these brief periods.

The normal processing of the PIQS 202 may be executed on every sample for which a pulse is deemed to be present. According to one embodiment, two instances of the PIQS 202 may receive their IR and Red inputs, from the SCS 206 and EAS 208 respectively, and their Qualified_Pulse_Periods may be processed by two corresponding instances of the PRCS 204. The instance that receives the ensemble-averaged waveforms also receives the Ensemble_Averaging_Weight. The Avg_Period input may be provided by the instance of the PRCS 204 that receives the non-ensemble-averaged Qualified_Pulse_Periods.

Figure 8:
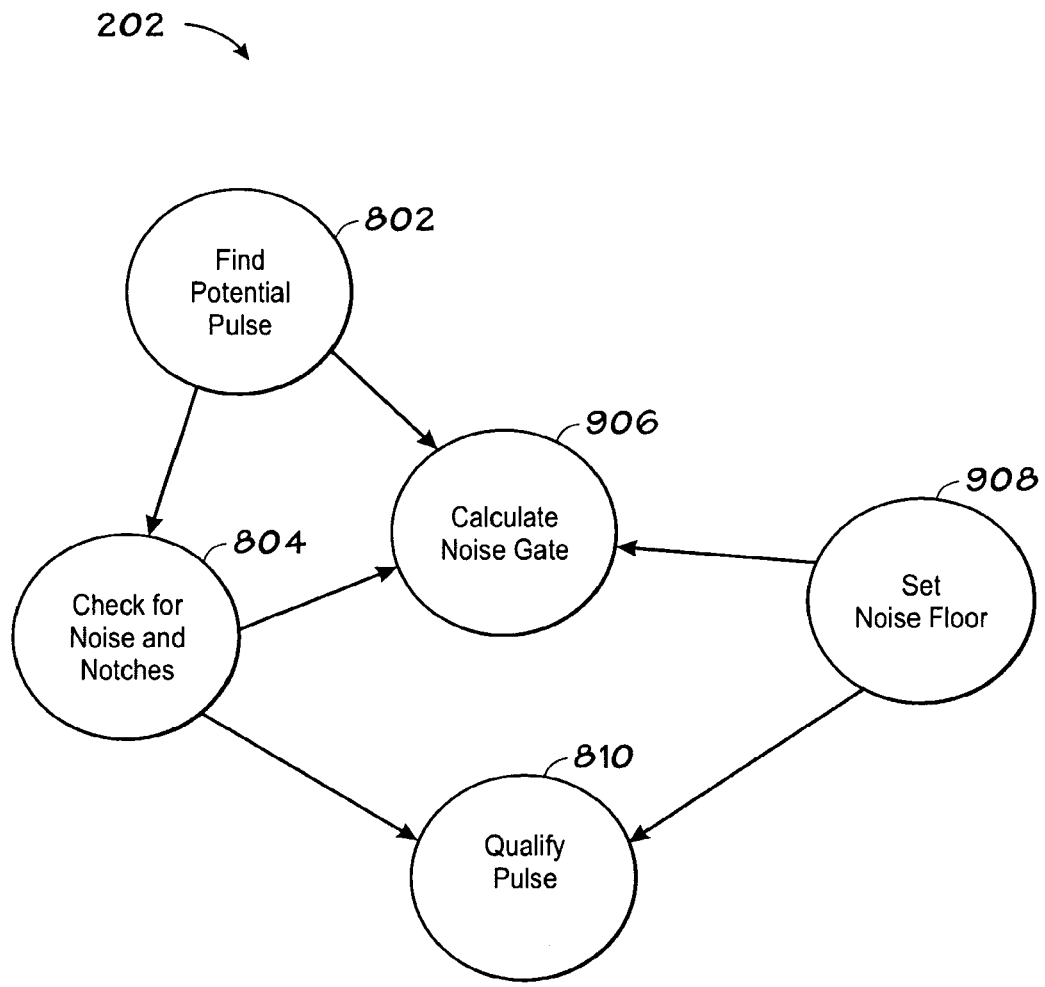
FIG. 8 is a context diagram of a pulse identification and qualification subsystem in accordance with an exemplary embodiment of the present invention.

FIG. 8 is a context diagram of the PIQS 202 in accordance with embodiments of the present invention. In the illustrated embodiment, the PIQS 202 includes a Find Potential Pulse transform 802, a Check For Noise and Notches transform 804, a Calculate Noise Gate transform 906, a Set Noise Floor transform 908, and a Qualify Pulse transform 810. A Reinitialize control is omitted for clarity. For each sample, the IR_Input_Waveform from the SCS 206 or EAS 208 may be processed by the Find Potential Pulse transform 802, which runs the state machine to identify potential pulses. Potential pulse parameters are fed to the Check For Noise and Notches transform 804. If a potential pulse is not ignored, the Qualify Pulse transform 810 is invoked.

The Calculate Noise Gate transform 806 may compute Mean_Square and Gated_RMS every non-ignored sample, and uses them to compute Noise_Gate when a potential pulse is found. The Set Noise Floor transform 808 may set Noise_Floors at startup and when Gains change, for use in calculating Noise_Gate and in correcting the Adjusted_RoR_Variance metric for the oximeter's hardware noise floor. The Qualify Pulse transform 810 may use values and buffers maintained by the Find Potential Pulse transform 802 to calculate the pulse parameters required by its pulse qualification criteria. The Qualify Pulse transform 810 may output Qualified_Pulse_Periods and set the Artifact, Beep_Now, Pulse_Rejected, and Pulse_Qualified flags as specified. Finally, it may reset the values maintained by the Find Potential Pulse transform 802, in preparation for the next pulse.

As set forth above, embodiments of the present invention include switching to alternative values of selected constants in the PIQS 202 that are used to identify and qualify pulses. Specifically, in one embodiment, the PIQS 202 switches to using the alternative constants when four consecutive pulses have been rejected (i.e., disqualified). The PIQS 202 then switches back to using the normal or original constants once three consecutive pulses have been qualified. In some embodiments, multiple alternative constants may be utilized. For example, different constants may be employed for different circumstances (e.g., six consecutive pulses have been rejected). Further, alternative constants may be switched directly without transitioning through use of the original constant.

TABLE 1 lists seven constants for which alternative values may be selected, along with two alternate values in accordance with embodiments of the present invention. These constants relate to settings for the noise gate (e.g., NGATE_GATED_RMS FRACTION, HALF_PERIOD_MULTIPLIER), characterizing pulse shapes (e.g., NOTCH_PERCENT_THRESH, SKEW_ADJUSTMENT_PER_SAMPLE), and setting thresholds for pulse quality (e.g., MIN_PER_VAR_FOR_REDUCED_ALT_SKEW_DIFF, NN_THRESH_DEFAULT, NN_THRESH_OFFSET). In one embodiment, these particular constants were selected, and their alternative values were determined, with the aid of genetic algorithms. Several large sets of pre-collected pulse oximetry data were manually analyzed to create files specifying best estimates of a true pulse rate over time. Genetic algorithms were then utilized to modify the values of one or more constants in the code for the PIQS 202. The modified code was then implemented. Pulse rates output by the modified code were compared to the manually determined pulse rates to quantify rate errors and posting time. These metrics were then combined into a fitness score for each code modification. The genetic algorithm then ranked the code modifications by their associated fitness scores, and continued to modify the constant values from the "fittest" modifications.

TABLE 1

| Name | Brief Description | Default Value Alternative Value |
|---|---|---|
| NGATE_GATED_RMS FRACTION | Multiplier used to scale the noise gate | 0.85 1.03, not used for head sensors |
| HALF_PERIOD_MULTIPLIER | Used to increase noise gate for pulse periods that are near half the average pulse period | 0.5 0.584, not used for head sensors |
| NOTCH_PERCENT_THRESH | Minimum percentage of recent potential pulses that must have been identified as dicrotic notches in order for a dicrotic notch to be concatenated with the next potential pulse rather than being submitted to pulse qualification by itself | 33 24, not used for head sensors |

TABLE 1-continued

| Name | Brief Description | Default Value Alternative Value |
|---|---|---|
| SKEW_ADJUSTMENT_PER_SAMPLE | Used to adjust a metric of pulse shape to compensate for the physiologic change in pulse shape that occurs as pulse rate changes | 0.0181 0.0151, always used for head sensors |
| MIN_PER_VAR_FOR_REDUCED_ALT_SKEW_DIFF | Used to reduce a metric of pulse-shape variability when pulse periods are also highly variable (arrhythmic). This pulse-shape-variability is one of several input metrics used by the subsystem's Pulse Qualification neural net to evaluate each pulse | 0.05 0.10, not used for head sensors |
| NN_THRESH_DEFUALT | Default threshold for the Pulse Qualification neural net's output in the absence of an average pulse period. | 0.5 0.06, not used for head sensors |
| NN_THRESH_OFFSET | Minimum threshold for the Pulse Qualification neural net's output if the current pulse period is very close to the average pulse period. | 0.4 0.03, not used for head sensors |

The trends of the various constants subject to modification by the genetic algorithm runs were manually analyzed to select those constants whose values were most strongly related to the fitness scores assigned to the various sets of modified constants. The final selection of constants, alternative values, and rules for using the alternative values were made based on the tradeoffs between the pulse rate errors and dropouts in these three databases. In one embodiment, a total of seven constants have alternative values provided out of roughly one-hundred constants in the pulse qualification code that were evaluated. Various conditions were found to benefit from alternative constants. In some instances, certain values were desirable when a head sensor was or was not being used.

Three bodies of data were analyzed to obtain the results set forth herein. A first body of data included tests on volunteers exposed to cold to induce poor perfusion in the fingers. This body of data is referred to as the cold-room database. The cold-room database includes 328 digits total from six study dates. Half of the digits has motion in these studies. A second body of data comprised files from 113 hospitalized patients exhibiting a variety of sensor sites, clinical conditions, and artifacts. This second body of data may be referred to as the hospital database. A third body of data included data from over 40 patients having various surgical procedures with sensors on their foreheads under conditions where venous pulsation had been observed. This third body of data may be referred to as the forehead/surgical database.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for analyzing pulse data, comprising:
receiving a signal at a pulse oximeter, the signal representative of light detected after being scattered by tissue and containing data representing a plurality of pulses;
performing a pulse qualification algorithm on at least a portion of the data using a processor of the pulse oximeter, the pulse qualification algorithm utilizing at least one constant; and
modifying the at least one constant using the processor when results obtained from performing the pulse qualification algorithm meet a condition.

2. The method of claim 1, comprising:
emitting the light from a light source of a sensor into the tissue;
detecting the light with a detector of the sensor after the light has been scattered by the tissue; and
generating the signal with the detector.

3. The method of claim 1, wherein the pulse qualification algorithm detects potential pulse amplitudes in the portion of the data.

4. The method of claim 3, wherein the condition comprises the potential pulse amplitudes being generally below a threshold.

5. The method of claim 1, wherein modifying the at least one constant comprises swapping a primary constant value with an alternate constant value.

6. The method of claim 1, comprising keeping a count of consecutive pulses rejected by the pulse qualification algorithm.

7. The method of claim 6, wherein the condition comprises the count of consecutive pulses rejected by the pulse qualification algorithm reaching a value.

8. The method of claim 1, comprising keeping a count of consecutive pulses qualified by the pulse qualification algorithm.

9. The method of claim 8, wherein the condition comprises the count of consecutive pulses qualified by the pulse qualification algorithm reaching a value.

10. A system for analyzing pulse data, comprising:
a receiver configured to receive a signal representative of light detected after being scattered by tissue, the signal containing data representing a plurality of pulses;
a filter configured to run a pulse qualification algorithm on at least a portion of the data, the pulse qualification algorithm comprising at least one constant; and a subsystem configured to modify the at least one constant when results obtained from running the pulse qualification algorithm meet a condition.

11. The system of claim 10, wherein the subsystem is configured to change a value of the at least one constant to an alternate value when the results obtained from running the pulse qualification algorithm meet the condition by indicating that a designated number of rejected pulses has been reached.

12. The system of claim 10, wherein the subsystem is configured to change a value of the at least one constant to an alternate value when the results obtained from running the pulse qualification algorithm meet the condition by indicating that a designated number of qualified pulses has been reached.

13. The system of claim 10, comprising a sensor, wherein the sensor comprises:

an emitter configured to emit light;

a detector configured to detect the light after being scattered by the tissue; and a signal generator configured to generate the signal.

14. The system of claim 10, wherein the subsystem is configured to change a value of the at least one constant to an alternate value when the results obtained from running the pulse qualification algorithm meet the condition by indicating that potential pulse amplitudes in the data are below a threshold.

15. A method for analyzing pulse data, comprising:

generating a signal at a sensor based on light scattered by blood perfused tissue and detected by the sensor, the signal containing data representing a plurality of pulses;

receiving the signal at a pulse oximeter;

performing a pulse qualification algorithm on at least a portion of the data using a processor of the pulse oximeter such that the pulse qualification algorithm identifies qualified and non-qualified pulses, the pulse qualification algorithm comprising at least one constant; and modifying the at least one constant using the processor based on results obtained from performing the pulse qualification algorithm meeting a condition.

16. The method of claim 15, wherein the condition is met when the results indicate that a designated number of consecutive non-qualified pulses have been identified.

17. The method of claim 15, wherein the condition is met when the results indicate that a designated number of consecutive qualified pulses have been identified.

18. The method of claim 15, wherein modifying the at least one constant comprises changing a value of the at least one constant to an alternative value associated with the condition.

19. The method of claim 15, wherein the condition is met when the results indicate that potential pulse amplitudes in the data are below a threshold.

20. The method of claim 15, comprising using the processor to calculate a pulse rate from periods of pulses identified as qualified by the pulse qualification algorithm.

* * * * *